(12) United States Patent
Nakano et al.

(10) Patent No.: US 10,435,394 B2
(45) Date of Patent: Oct. 8, 2019

(54) PLANT GROWTH-PROMOTION AGENT AND METHOD FOR PROMOTING PLANT GROWTH

(71) Applicant: RIKEN, Wako-shi, Saitama (JP)

(72) Inventors: Takeshi Nakano, Wako (JP); Tadao Asami, Wako (JP); Hiroyuki Osada, Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 15/517,612

(22) PCT Filed: Oct. 7, 2015

(86) PCT No.: PCT/JP2015/078454
§ 371 (c)(1),
(2) Date: Apr. 7, 2017

(87) PCT Pub. No.: WO2016/056581
PCT Pub. Date: Apr. 14, 2016

(65) Prior Publication Data
US 2017/0305886 A1 Oct. 26, 2017

(30) Foreign Application Priority Data
Oct. 8, 2014 (JP) .................................. 2014-207442

(51) Int. Cl.
| | |
|---|---|
| A01N 43/36 | (2006.01) |
| A01N 43/40 | (2006.01) |
| A01N 43/50 | (2006.01) |
| A01N 43/60 | (2006.01) |
| A01N 43/647 | (2006.01) |
| A01N 43/653 | (2006.01) |
| A01N 43/84 | (2006.01) |
| A01N 43/30 | (2006.01) |
| A01N 43/38 | (2006.01) |
| A01N 33/08 | (2006.01) |
| A01N 43/32 | (2006.01) |
| C07D 405/06 | (2006.01) |
| A01G 7/06 | (2006.01) |
| C07D 295/03 | (2006.01) |
| C07D 295/073 | (2006.01) |
| C07D 295/096 | (2006.01) |
| C07D 317/58 | (2006.01) |
| C07D 319/18 | (2006.01) |

(52) U.S. Cl.
CPC ............ *C07D 405/06* (2013.01); *A01G 7/06* (2013.01); *A01N 33/08* (2013.01); *A01N 43/30* (2013.01); *A01N 43/32* (2013.01); *A01N 43/36* (2013.01); *A01N 43/38* (2013.01); *A01N 43/40* (2013.01); *A01N 43/50* (2013.01); *A01N 43/60* (2013.01); *A01N 43/647* (2013.01); *A01N 43/653* (2013.01); *A01N 43/84* (2013.01); *C07D 295/03* (2013.01); *C07D 295/073* (2013.01); *C07D 295/096* (2013.01); *C07D 317/58* (2013.01); *C07D 319/18* (2013.01)

(58) Field of Classification Search
None
See application file for complete search history.

(56) References Cited

U.S. PATENT DOCUMENTS

| | | | |
|---|---|---|---|
| 6,207,665 B1 | 3/2001 | Bauman et al. | |
| 2010/0324030 A1 | 12/2010 | Dale et al. | |
| 2013/0196973 A1 | 8/2013 | Abeywardane et al. | |

FOREIGN PATENT DOCUMENTS

| | | |
|---|---|---|
| JP | 61-212504 A | 9/1986 |
| JP | 62-167710 A | 7/1987 |
| JP | 11-255607 A | 9/1999 |
| JP | 2002-500653 A | 1/2002 |

(Continued)

OTHER PUBLICATIONS

Votava et al.( Pharmacological research on synthetic uterotonics. II. Substituted N-benzylpiperidines and 3,4-dimethoxybenzylamines, Chekhoslovatskaya Fiziologiya (1954), 3, 426-31) (Year: 1954).*
International Search Report and Written Opinion dated Dec. 8, 2015, in PCT/JP2015/078454.
Database CAS Registry No. 1556391-35-5, Feb. 26, 2014, retrieved from STN International online on Dec. 1, 2015.
Database CAS Registry No. 1307399-14-9, Jun. 8, 2011, retrieved from STN International online on Dec. 1, 2015.

(Continued)

*Primary Examiner* — Alton N Pryor
(74) *Attorney, Agent, or Firm* — Foley & Lardner LLP

(57) ABSTRACT

The present invention concerns: a plant growth-promoting agent comprising a compound represented by Formula (I) or a salt thereof:

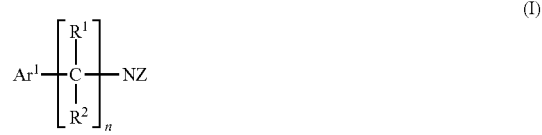

(I)

wherein $Ar^1$ represents a substituted or unsubstituted phenyl group, NZ represents a nitrogen-containing heterocyclic ring group or an acyclic nitrogen-containing group having a partial structure of the nitrogen-containing heterocyclic ring group, n is 0, 1, or 2, $R^1$ and $R^2$ each represent a hydrogen atom, a substituted or unsubstituted $C_{1-3}$-alkyl group, a cyano group, or a carboxyl group, $R^1$ and $R^2$ may together form an oxo group, and when n is 2, $R^1$ or $R^2$ may be the same or different; and a method for promoting plant growth using the plant growth-promoting agent.

14 Claims, 18 Drawing Sheets

(56) References Cited

FOREIGN PATENT DOCUMENTS

| JP | 2002-503239 A | 1/2002 |
|---|---|---|
| JP | 2009-511530 A | 3/2009 |
| JP | 2009-528976 A | 8/2009 |
| JP | 2014-511826 A | 5/2014 |
| WO | WO 98/54115 A1 | 12/1998 |
| WO | WO 2008/096189 A2 | 8/2008 |
| WO | WO 2010/001563 A1 | 1/2010 |
| WO | WO 2013/171092 A1 | 11/2013 |
| WO | WO 2015/171092 A1 | 11/2013 |
| WO | WO 2014/005122 A2 | 1/2014 |

OTHER PUBLICATIONS

Phutdhawong et al., "Synthesis of 3-indolylacetamide derivatives and evaluation of their plant growth regulator activity," Maejo International Journal of Science and Technology, Jul. 2014, 8(2):181-189.

* cited by examiner

PLANT GROWTH-PROMOTION AGENT AND METHOD FOR PROMOTING PLANT GROWTH

CROSS-REFERENCE TO RELATED APPLICATIONS

This application is a National Stage application of PCT/JP2015/078454, filed Oct. 7, 2015, which claims priority from Japanese application JP 2014-207442, filed Oct. 8, 2014.

TECHNICAL FIELD

The present invention relates to a plant growth-promoting agent and a method for promoting plant growth.

BACKGROUND ART

Hitherto, plant growth-promoting agents having effects of, for example, promoting rhizogenesis of plants, preventing lodging, improving yield, cold resistance, and green color, enhancing good seedling, increasing the number of tiller buds (branches), promoting organ growth have been used in order to improve yields of plants.

For example, Patent Document 1 discloses that a tetrazoyloxime derivative is a useful plant growth-promoting agent.

In addition, Patent Document 2 discloses a composition containing a choline and hydroxyisoxazole for promoting rhizogenesis and good seedling of rice, and Patent Document 3 suggests an agent for promoting good seedling of rice, which contains 3-hydroxypyrazine or a derivative thereof as an active ingredient.

The substances disclosed in Patent Documents 1 to 3, however, have structures that totally differ from the structures of the compounds used as active ingredients in the present invention.

Among compounds used as active ingredients in the present invention, 1-piperonylpiperazine (1-(3,4-methylenedioxybenzyl)piperazine) and many analogs thereof, which are 1-substituted piperazine derivatives and analogs thereof, are used as manufacturing starting materials and commercially available (e.g., Patent Documents 4 and 5).

However, there has been no report demonstrating that the compounds used as active ingredients in the present invention have plant growth promoting effects.

PRIOR ART DOCUMENTS

Patent Documents

Patent Document 1: WO 2010/001563
Patent Document 2: JP S61-212504 (A) (1986)
Patent Document 3: JP S62-167710 (A) (1987)
Patent Document 4: JP 2002-503239 (A)
Patent Document 5: WO 2014/005122

SUMMARY OF THE INVENTION

Objects to be Attained by the Invention

It is an object of the present invention to provide a plant growth-promoting agent having a basic structure that differs from basic structures of conventional plant growth-promoting agents, and a method for promoting plant growth using such plant growth-promoting agent.

Means for Attaining the Objects

The present invention is summarized as follows.
(1) A plant growth-promoting agent comprising a compound represented by Formula (I) or a salt thereof:

wherein $Ar^1$ represents a substituted or unsubstituted phenyl group;
NZ represents a substituted or unsubstituted nitrogen-containing heterocyclic ring group having 1 or 2 nitrogen atoms, which is bound to $C(R^1)(R^2)$ or $Ar^1$ via a nitrogen atom, or a group represented by Formula (II):

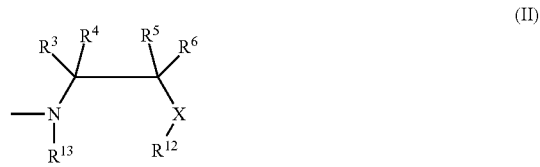

wherein X represents $NR^{11}$ (where $R^{11}$ represents a hydrogen atom or a substituted or unsubstituted $C_{1-3}$-alkyl group), an oxygen atom, a sulfur atom, $-SO_2-$, $-SO-$, a methylene group, or a direct bond;
$R^3$, $R^4$, $R^5$ and $R^6$ each represent a hydrogen atom or a methyl group;
$R^3$ and $R^4$ and/or $R^5$ and $R^6$ may together form an oxo group;
$R^{12}$ and $R^{13}$ each represent a hydrogen atom or a substituted or unsubstituted $C_{1-3}$-alkyl group;
n is 0, 1, or 2; and
$R^1$ and $R^2$ each represent a hydrogen atom, a substituted or unsubstituted $C_{1-3}$-alkyl group, a cyano group, or a carboxyl group, $R^1$ and $R^2$ may together form an oxo group, and when n is 2, $R^1$ or $R^2$ may be the same or different.
(2) The plant growth-promoting agent according to item (1) above, wherein the compound represented by Formula (I) or a salt thereof is a compound represented by Formula (Ia) or a salt thereof:

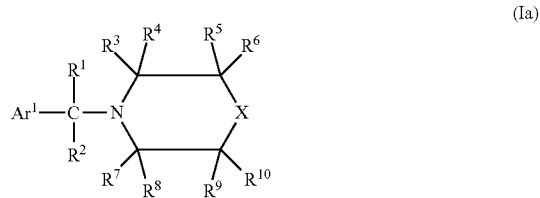

wherein $Ar^1$, $R^1$, and $R^2$ are as defined above with respect to Formula (I) in claim 1;
X represents $NR^{11}$ (where $R^{11}$ represents a hydrogen atom or a substituted or unsubstituted $C_{1-3}$-alkyl group), an oxygen atom, a sulfur atom, $-SO_2-$, $-SO-$, a methylene group, or a direct bond;

$R^3$, $R^4$, $R^5$, $R^6$, $R^7$, $R^8$, $R^9$, and $R^{10}$ each represent a hydrogen atom or a methyl group; and $R^3$ and $R^4$, $R^5$ and $R^6$, $R^7$ and $R^8$, and/or $R^9$ and $R^{10}$ may together form an oxo group.

(3) The plant growth-promoting agent according to item (1) above, wherein $R^1$ and $R^2$ each represent a hydrogen atom, and n is 1 or 2 in Formula (I).

(4) The plant growth-promoting agent according to item (2) above, wherein $R^1$ and $R^2$ each represent a hydrogen atom in Formula (Ia).

(5) The plant growth-promoting agent according to any one of items (1) to (4) above, wherein $Ar^1$ is a phenyl group substituted with one methylenedioxy group or one or two methoxy groups in Formula (I) or (Ia).

(6) The plant growth-promoting agent according to any one of items (1) and (3) to (5) above, wherein NZ represents a saturated nitrogen-containing heterocyclic ring group in Formula (I).

(7) A compound represented by Formula (III) or a salt thereof:

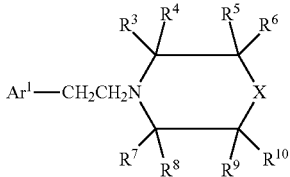

(III)

wherein $Ar^1$ represents a substituted or unsubstituted phenyl group;

$R^3$, $R^4$, $R^5$, $R^6$, $R^7$, $R^8$, $R^9$, and $R^{10}$ each represent a hydrogen atom or a methyl group; and $R^3$ and $R^4$, $R^5$ and $R^6$, $R^7$ and $R^8$, and/or $R^9$ and $R^{10}$ may together form an oxo group.

(8) A compound represented by Formula (IV) or a salt thereof:

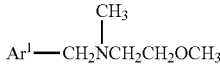

(IV)

wherein $Ar^1$ represents a substituted or unsubstituted phenyl group.

(9) A method for promoting plant growth, comprising bringing a plant, plant cells, a plant tissue, or plant seeds into contact with the plant growth-promoting agent according to any one of items (1) to (6) above.

Effects of the Invention

The plant growth-promoting agent of the present invention comprises, as an active ingredient, an N-substituted heterocyclic ring having a basic structure differing from that of a conventional plant growth-promoting agent or an acyclic nitrogen-containing compound having a partial structure thereof. Thus, such agent can be applied to a wide variety of plants.

EMBODIMENTS FOR IMPLEMENTING THE INVENTION

Figure 1:
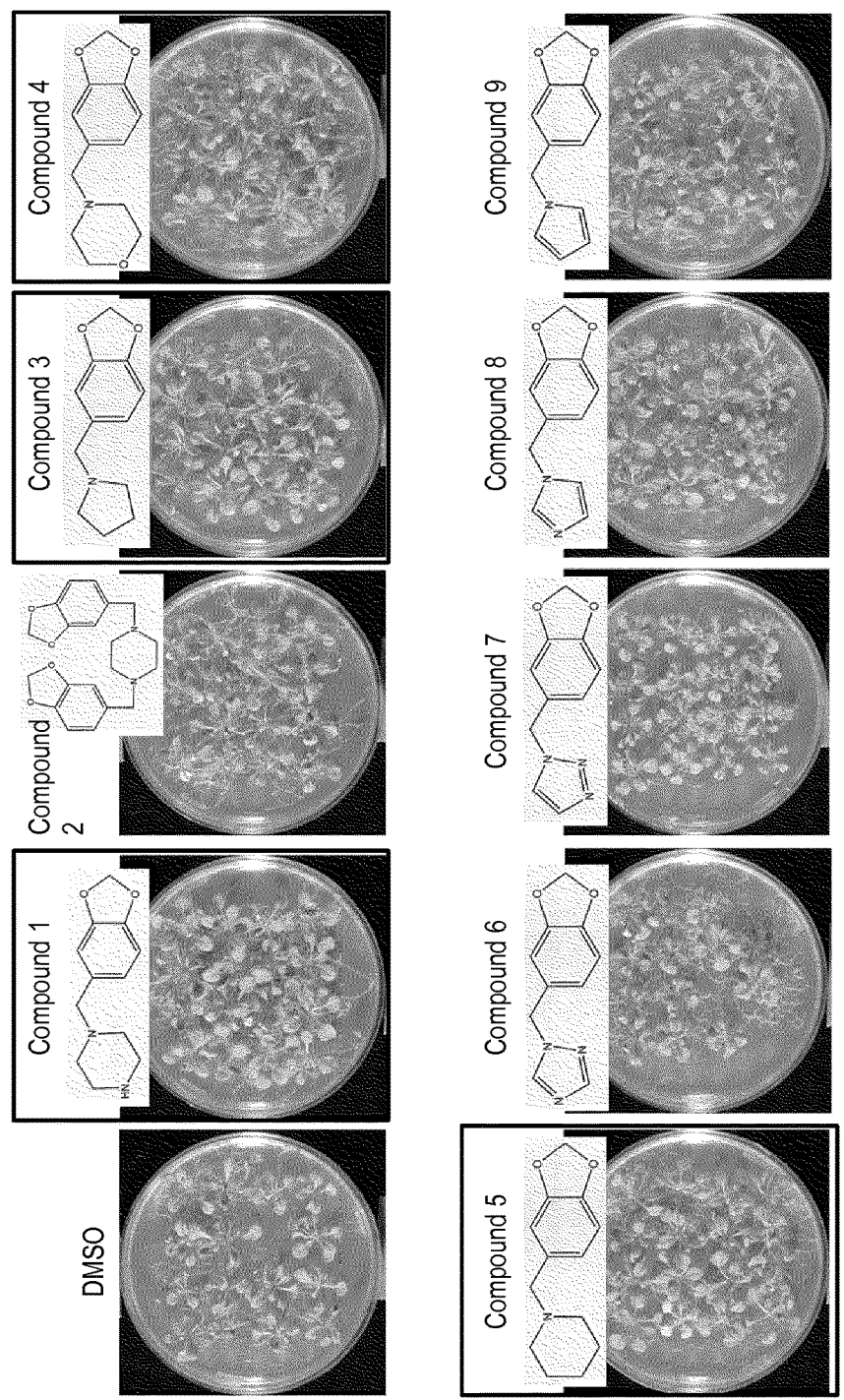
FIG. 1 shows the results of the plant growth promoting activity test using *Arabidopsis*.

Hereafter, the present invention is described in detail.

Examples of a substituent of the substituted phenyl group represented by $Ar^1$ in Formulae (I), (Ia), (III), and (IV) include: $C_{1-6}$-alkoxy groups such as a methoxy group, an ethoxy group, a propoxy group, and an isopropoxy group; substituted or unsubstituted alkylenedioxy groups such as a methylenedioxy group, an ethylenedioxy group, a trimethylenedioxy group, a difluoromethylenedioxy group, and a dichloromethylenedioxy group; and halogen atoms such as a fluorine atom, a chlorine atom, a bromine atom, and an iodine atom. A phenyl group represented by $Ar^1$ may be substituted with one or two substituents described above or other substituents. It is preferable for a phenyl group represented by $Ar^1$ to be substituted with one methylenedioxy group or one or two methoxy groups.

Examples of a phenyl group represented by $Ar^1$ include a 3,4-methylenedioxyphenyl group (a 1,3-benzodioxol-5-yl group), a 2,3-methylenedioxyphenyl group (a 1,3-benzodioxol-4-yl group), a 3,4-(a difluoromethylenedioxy)phenyl group (a 2,2-difluoro-1,3-benzodioxol-5-yl group), a 2,3-(difluoromethylenedioxy)phenyl group (a 2,2-difluoro-1,3- benzodioxol-4-yl group), a 3,4-methylenedioxy-5-methoxyphenyl group (a 7-methoxy-1,3-benzodioxol-5-yl group), a 2-methoxyphenyl group, a 3-methoxyphenyl group, a 4-methoxyphenyl group, a 3,4-dimethoxyphenyl group, a 2,3-dimethoxyphenyl group, a 2-chlorophenyl group, a 3-chlorophenyl group, a 4-chlorophenyl group, a 2,4-dichlorophenyl group, and a 2,4,5-trichlorophenyl group. Preferable examples thereof include a 3,4-methylenedioxyphenyl group (a 1,3-benzodioxol-5-yl group), a 2,3-methylenedioxyphenyl group (a 1,3-benzodioxol-4-yl group), a 2-methoxyphenyl group, a 3-methoxyphenyl group, a 4-methoxyphenyl group, a 3,4-dimethoxyphenyl group, and a 2,3-dimethoxyphenyl group.

The nitrogen-containing heterocyclic ring group represented by NZ in Formula (I) is not limited as long as it is bound to C($R^1$)($R^2$) or $Ar^1$ (when n is 0 in Formula (I)) Via a nitrogen atom and it has one or two nitrogen atoms. Examples thereof include: saturated nitrogen-containing heterocyclic ring groups such as a 1-piperazinyl group, a 1-pyrrolidinyl group, a piperazino group, a morpholino group, a 1,1-dioxidethiomorpholino group, and a perhydro-1,4-thiazine-4-yl group; unsaturated nitrogen-containing heterocyclic ring groups such as a 1-pyrrolyl group, a 1-imidazolyl group, a 1-pyrazolyl group, a 1H-1,2,3-triazole-1-yl group, and a 1H-1,2,4-triazole-1-yl group. Preferable examples thereof include saturated nitrogen-containing heterocyclic ring groups such as a 1-piperazinyl group, a 1-pyrrolidinyl group, a piperazino group, a morpholino group, a 1,1-dioxidethiomorpholino group, and a perhydro-1,4-thiazine-4-yl group. The nitrogen-containing heterocyclic ring group may be substituted with at least one substituent selected from the group consisting of, for example, $C_{1-5}$-alkyl groups such as a methyl group, an ethyl group, a propyl group, an isopropyl group, a butyl group, an isobutyl group, a sec-butyl group, a tert-butyl group, a pentyl group, and an isopentyl group, $C_{1-6}$-alkoxy groups such as a methoxy group, an ethoxy group, a propoxy group, and an isopropoxy group, and halogen atoms such as a fluorine atom, a chlorine atom, a bromine atom, and an iodine atom. An example of the substituted nitrogen-containing heterocyclic ring group is a 4-methyl-1-piperazinyl group.

Examples of a $C_{1-3}$-alkyl group represented by $R^1$, $R^2$, $R^{11}$, $R^{12}$, or $R^{13}$ in Formula (I), (Ia), or (II) include a methyl group, an ethyl group, a propyl group, and an isopropyl group. These $C_{1-3}$-alkyl groups may be substituted with at least one substituent selected from the group consisting of, for example, an amino group, a hydroxyl group, a carboxyl group, a cyano group, a halogen atom (e.g., a fluorine atom, a chlorine atom, a bromine atom, or an iodine atom), and a nitro group. $R^1$ and $R^2$ may together form an oxo group. Preferably, W and $R^2$ each represent a hydrogen atom. Preferably, $R^{12}$ and $R^{13}$ each represent a methyl group.

Preferably, n is 1 or 2 in Formula (I).

Preferably, the compound represented by Formula (I) or a salt thereof is a compound, in which a nitrogen-containing heterocyclic ring group represented by NZ is a saturated nitrogen-containing heterocyclic ring group and n is 1 or 2, such as a compound represented by Formula (Ia), a compound, wherein a nitrogen-containing heterocyclic ring group represented by NZ is an acyclic nitrogen-containing group represented by Formula (II), or a salt of thereof.

Preferably, $R^3$, $R^4$, $R^5$, $R^6$, $R^7$, $R^8$, $R^9$, and $R^{10}$ in Formulae (Ia) and (III) and $R^3$, $R^4$, $R^5$, and $R^6$ in Formula (II) each represent a hydrogen atom.

Examples of a salt of the compound represented by Formula (I), (Ia), (III), or (IV) include salts with inorganic acids, such as hydrochloric acid, sulfuric acid, phosphoric acid, hydrobromic acid, hydroiodic acid, nitric acid, pyrosulfuric acid, and metaphosphoric acid, and salts with organic acids, such as citric acid, benzoic acid, acetic acid, propionic acid, fumaric acid, maleic acid, tartaric acid, succinic acid, sulfonic acid (e.g., methanesulfonic acid, p-toluenesulfonic acid, or naphthalenesulfonic acid), and amino acid (e.g., glutamic acid).

The compounds represented by Formula (I) can be produced in accordance with a conventional technique, such as the method in "Reaction scheme 1" (n=1 or 2) described in JP 2002-503239 A or the method described in M. Nishiyama, et al., Tetrahedron Letters, 39 (1998), 617-620 (n=0), in the manner described below:

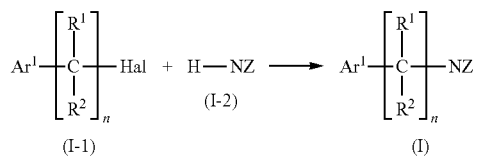

(wherein $Ar^1$, NZ, $R^1$, $R^2$, and n are as defined above; and Hal represents a halogen atom (a chlorine, bromine, or iodine atom)).

The compounds represented by Formula (I), wherein $R^1$=$R^2$=H, n=1, can be produced in accordance with the method described in M. Haniti S. A. Hamid, et al., Tetrahedron Letters, 48 (2007), 8263-8265 with the use of [Ru(cymene)Cl$_2$]$_2$ and diphosphine as catalysts in the manner described below:

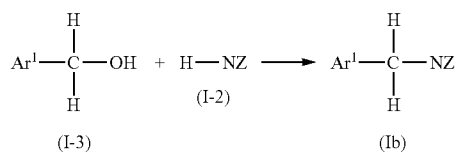

(wherein $Ar^1$ and NZ are as defined above).

In addition, the compounds represented by Formula (I), wherein $R^1$=$R^2$=H, n=1, can be produced in accordance with the method described in WO 2014/005122 by reacting a compound (I-4) and a compound (I-2) in the presence of sodium triacetoxyborohydride in the manner described below.

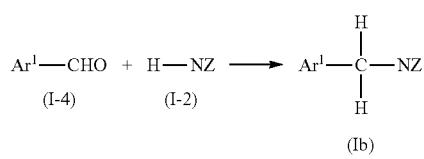

(wherein $Ar^1$ and NZ are as defined above).

Products that can be obtained in the manner described above may be purified in accordance with a conventional technique, such as column chromatography using silica gel or the like as a carrier, or recrystallization using methanol, ethanol, chloroform, dimethylsulfoxide, water, or the like. Examples of eluting solvents used for column chromatography include methanol, ethanol, chloroform, acetone, hexane, dichloromethane, ethyl acetate, and a solvent mixture of any thereof.

Among the compounds represented by Formula (I) or (Ia), commercially available compounds can be used in the present invention.

The expression "plant growth promotion" according to the present invention refers to not only growth promotion after sprouting but also sprouting promotion. The expression "sprouting promotion" refers to increasing the sprouting rate (i.e., the percentage of sprouting seeds among sown seeds) and decreasing the time required for sprouting from seeds. The expression "growth promotion after sprouting" refers to stem elongation/enlargement, root elongation/enlargement, leaf growth, branching promotion, salt tolerance enhancement, and the like.

A subject treated with the plant growth-promoting agent of the present invention is not limited as long as it is a plant. Examples thereof include plant seeds, calluses, young leaves formed immediately after sprouting, and a growing plant.

Examples of plants to which the present invention is applicable include, but are not particularly limited to: vegetables of the family Cucurbitaceae, such as cucumber, melon, pumpkin, and watermelon; vegetables of the family Solanaceae such as eggplant, tomato, bell pepper, and pepper; vegetables of the family Liliaceae such as onion and green onion; vegetables of the family Brassicaceae such as Japanese radish, turnip, Chinese cabbage, cabbage, cauliflower, broccoli, and mustard; vegetables of the family Apiaceae such as carrot and celery; vegetables of the family Asteraceae such as burdock, lettuce, and crown daisy; vegetables of the family Lamiaceae such as Japanese basil; vegetables of the family Lamiaceae such as quinoa and spinach; vegetables of the family Leguminosae such as red bean, soybean, pea, and kidney bean; flowering plants of the family Ranunculaceae such as Delphinium elatum; flowering plants of the family Violaceae such as pansy; flowering plants of the family Campanulaceae such as lobelia; grain of the family Polygonaceae such as buckwheat; grain of the family Gramineae such as wheat, barley, oat, rye, rice, and proso; fruits of the family Rosaceae such as apple, pear, cherry, and peach; fruits of the family Theaceae such as kiwifruit; fruits of the family Vitaceae such as grape; plants of the family Fagaceae such as Japanese beech and sawthorn oak; and plants of the family cedar and Japanese cypress.

The method for promoting plant growth according to the present invention comprises bringing the compound represented by Formula (I) or a salt thereof into contact with the above plants. The method and embodiments of carrying out the method are not limited as long as the compound represented by Formula (I) or a salt thereof can be brought into contact with a plant or seeds thereof.

The plant growth-promoting agent of the present invention can be directly used in the form of a powder (solid) or it can be dissolved or dispersed in a solvent so as to be used in the form of a solution or dispersion liquid. Type of a solvent is not limited unless the solvent is harmful to plants.

When the plant growth-promoting agent is used in the powder form, it may be directly sprinkled on soil for cultivation, or if necessary, it may be mixed in advance with soil for cultivation. When seeds are sown on culture soil, the plant growth-promoting agent may be mixed in advance with culture soil before sowing or the plant growth-promoting agent mixed with culture soil may be sprinkled after sowing. Also when the plant growth-promoting agent of the present invention is applied to sprouting plants, it may be mixed in advance with culture soil before planting the plants, or the plant growth-promoting agent of the present invention mixed with culture soil may be sprinkled after planting.

When the plant growth-promoting agent of the present invention in the form of an aqueous solution is used, seeds or sprouting plants can be immersed in an aqueous solution containing the compound represented by Formula (I) or a salt thereof. Alternatively, the aqueous solution can be sprayed to seeds or sprouting plants, or it may be sprayed to, mixed with, or supplied to soil for cultivation. Any means such as a water port, a sprinkler, or atomizer can be used in the above mode.

The culture soil of the present invention includes not only soil or sand but also a base such as absorbent cotton or sponge, which allows seeds to sprout and plants to grow.

When plant seeds are immersed in the above aqueous solution, it is desirable to continuously or intermittently immerse them while constantly or intermittently keeping parts other than roots outside of the aqueous solution, which allows favorable transpiration effects and growth promotion.

It is also possible to bring plant seeds into contact with the plant growth-promoting agent of the present invention in a rotatable container such as a rotary drum used for production of curl sprouts. In such case, roots of plant seeds are intermittently immersed in the plant growth-promoting agent while parts other than roots are also intermittently kept outside of the aqueous solution. It is appropriate to operate the rotary drum under conditions at, for example, a rate of 1 rotation per minute.

The amount of the plant growth-promoting agent of the present invention to be applied may be adequately adjusted depending on types of sprouts, growing conditions, intervals of application, frequency of application, types of preparations, and the like.

When the plant growth-promoting agent in the form of an aqueous solution is applied to soil for cultivation before sowing, it is preferable to add the compound represented by Formula (I) or a salt thereof to 80 to 120 mL of soil for cultivation at a concentration of, for example, 5 to 5000 ppm and preferably 60 to 600 ppm per 100 $cm^3$ of soil for cultivation. When the plant growth-promoting agent in the form of a powder is mixed, it is mixed to result in a concentration of, for example, 7 to 460 mg and preferably 10 to 400 mg per 100 $cm^3$ of soil for cultivation.

When the plant growth-promoting agent in the form of an aqueous solution is applied to sown seeds of a plant or seedlings of a plant in the raising seedling stage, the compound represented by Formula (I) or a salt thereof can be directly applied to the plant at a concentration of, for example, 5 to 5000 ppm and preferably 60 to 600 ppm. The amount aqueous solution to be sprayed can be appropriately changed depending on types of plant seeds. In general, it can be set to a level corresponding to 4 to 12 mL/100 $cm^2$ and preferably 8 to 10 mL/100 $cm^2$ per day. It is also possible to divide the amount corresponding to such concentration into several amounts. The frequency of spraying may be usually 6 times and preferably 3 times a day.

The mode of spraying is not particularly limited. For example, an apparatus such as an atomizer, a sprinkler, or a spray for spraying an agriculture chemical can be used. In addition, when the plant growth-promoting agent is sprayed to or mixed with soil for cultivation of plants, it is sprayed at a concentration of, for example, 1 to 5000 mg/100 $cm^3$ and preferably 6 to 600 mg/100 $cm^3$. It is also possible to divide the amount corresponding to such concentration into several amounts. When it is sprayed in several divided amounts, it is sprayed usually 1 to 3 times a day for 5 to 15 days and preferably 1 or 2 times a day for 8 to 12 days.

The plant and the aqueous solution may be maintained at 20° C. to 35° C. and preferably 25° C. to 30° C. in a growing environment. The reason why temperature is set to not less than 20° C. is to allow sufficient absorption of the plant growth-promoting agent of the present invention. In addition, the reason why temperature is set to not more than 35° C. is to allow sufficient absorption of the plant growth-promoting agent of the present invention and avoid brownish discoloration, withering, and the like.

It is possible to add other components as additives to the compound represented by Formula (I) or a salt thereof for the plant growth-promoting agent of the present invention. Any additive may be used unless it inhibits plant growth promotion.

The compound represented by Formula (Ia) or a salt thereof may induce a callus when used in combination with a compound represented by the following formula, which is synthetic auxin, or a salt thereof:

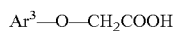

wherein $Ar^3$ represents a phenyl group substituted with 1 to 3 halogen atoms. Note that the compound does not induce a callus without the use of such synthetic auxin and exhibits plant growth promoting effects.

Either a fertilizer or a culture soil containing the plant growth-promoting agent of the present invention can be used. In addition, a plant cultivation kit including plant seeds and a fertilizer and/or culture soil containing the plant growth-promoting agent of the present invention can be used.

This description includes part or all of the content as disclosed in the description and/or drawings of Japanese Patent Application No. 2014-207442, which is a priority document of the present application.

EXAMPLES

Hereafter, the present invention is described in greater detail with reference to the examples, although the technical scope of the present invention is not limited to these examples.

(Example 1) Plant Growth Promoting Effects of the Plant Growth-Promoting Agent of the Present Invention Plant growth promoting effects of the plant growth-promoting agent of the present invention were examined using the compounds described below.

A. Test Compound (1) Compound 1 (CAS Registration No. 32231-06-4; hereafter sometimes referred to as "PPZ")

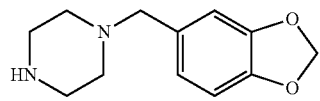

(2) Compound 2 (CAS Registration No. 55436-41-4)

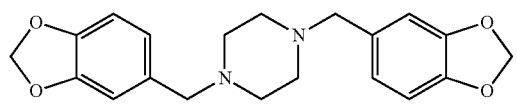 [SMILES: c1cc2c(cc1CN1CCN(Cc3ccc4c(c3)OCO4)CC1)OCO2]

(3) Compound 3 (CAS Registration No. 79089-40-0)

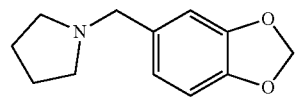 [SMILES: c1cc2c(cc1CN1CCCC1)OCO2]

(4) Compound 4 (CAS Registration No. 79089-66-0; the compound described in M. Haniti S. A. Hamid, et al., Tetrahedron Letters, 48 (2007), 8263-8265)

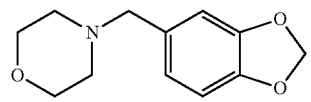 [SMILES: c1cc2c(cc1CN1CCOCC1)OCO2]

(5) Compound 5 (CAS Registration No. 79089-28-4)

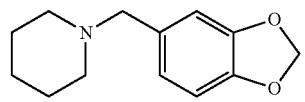 [SMILES: c1cc2c(cc1CN1CCCCC1)OCO2]

(6) Compound 6 (CAS Registration No. 106535-17-5)

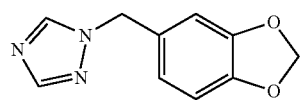 [SMILES: c1ncn(Cc2ccc3c(c2)OCO3)n1]

(7) Compound 7

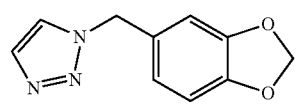 [SMILES: c1cn(Cc2ccc3c(c2)OCO3)nn1]

(8) Compound 8 (CAS Registration No. 56643-77-7; the compound described in Erick Cuevas-Yanez, et al., Tetrahedron, 60 (2004), 9391-9396)

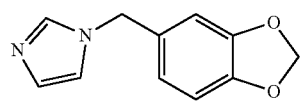 [SMILES: c1cn(Cc2ccc3c(c2)OCO3)cn1]

(9) Compound 9 (CAS Registration No. 1247355-09-4; the compound described in Indubhusan Deb, et al.; Chemical Communications, 2011, 47, 6473-6475)

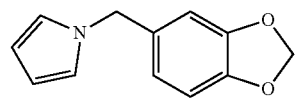 [SMILES: c1ccn(Cc2ccc3c(c2)OCO3)c1]

(10) Compound 10 (CAS Registration No. 22792-30-9; the compound described in Steven V. Ley, et al., J. Chem. Soc., Perkin Trans. 15 (1998), 2239-2242; Amine 10 in Eur. J. Org. Chem., 5144-5148 (2014))

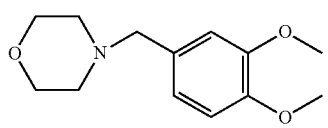 [SMILES: COc1ccc(CN2CCOCC2)cc1OC]

(11) Compound 11 (CAS Registration No. 55500-12-4; Compound 26 described in Johannes A. Burkhard, et al., Angew. Chem. Int. Ed, 49 (2010), 3524-3527)

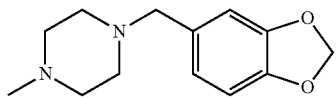 [SMILES: CN1CCN(Cc2ccc3c(c2)OCO3)CC1]

(12) Compound 12 (CAS Registration No. 414876-42-9; Compound 31 described in Johannes A. Burkhard, et al., Angew. Chem. Int. Ed, 49 (2010), 3524-3527)

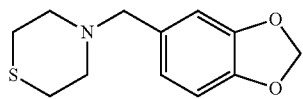 [SMILES: c1cc2c(cc1CN1CCSCC1)OCO2]

(13) Compound 13 (CAS Registration No. 34274-05-0; Compound 35 described in WO2014/005122)

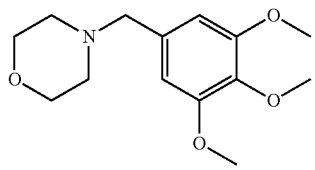 [SMILES: COc1cc(CN2CCOCC2)cc(OC)c1OC]

(14) Compound 14 (CAS Registration No. 1021359-42-1; the compound described in Table 7 of J. Org. Chem., 73, 3047-3062 (2008))

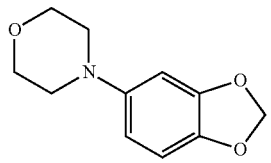 [SMILES: c1cc2c(cc1N1CCOCC1)OCO2]

(15) Compound 15 (CAS Registration No. 1504988-49-1; commercially available (Aurora Building Blocks and FCH Group Reagents for Synthesis))

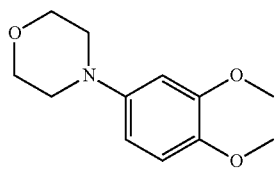 [SMILES: COc1ccc(N2CCOCC2)cc1OC]

(16) Compound 16 (the compound of Example 4)

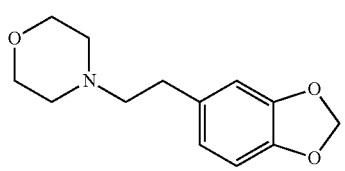 [SMILES: c1cc2c(cc1CCN1CCOCC1)OCO2]

(17) Compound 17 (the compound of Example 5)

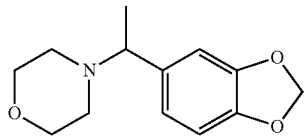 [SMILES: CC(c1ccc2c(c1)OCO2)N1CCOCC1]

(18) Compound 18 (CAS Registration No. 1529658-70-5; Compound 44 described in WO2014/005122)

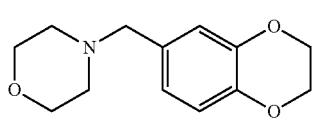 [SMILES: c1cc2c(cc1CN1CCOCC1)OCCO2]

(19) Compound 19 (CAS Registration No. 10316-00-4; the compound of entry 9 in table 2 of Organometallics, 32, 7440-7444 (2013))

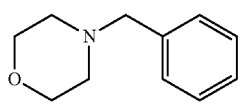 [SMILES: c1ccc(CN2CCOCC2)cc1]

(20) Compound 20 (CAS Registration No. 212392-57-9; the compound described in J. Chem. Soc., Perkin Trans. 1, 2239-2241 (1998))

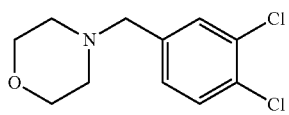 [SMILES: Clc1ccc(CN2CCOCC2)cc1Cl]

(21) Compound 21 (CAS Registration No. 477858-19-8; Compound 32 described in Johannes A. Burkhard, et al., Angew. Chem. Int. Ed, 49 (2010), 3524-3527)

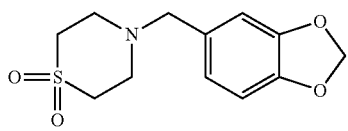 [SMILES: O=S1(=O)CCN(Cc2ccc3c(c2)OCO3)CC1]

(22) Compound 22 (the compound of Example 6)

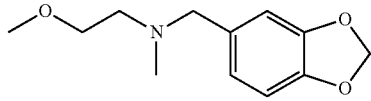 [SMILES: COCCN(C)Cc1ccc2c(c1)OCO2]

(23) Compound 23 (CAS Registration No. 65019-15-0; Compound 3i described in J. Org. Chem., 73, 7175-7180 (2008))

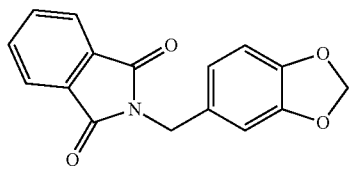 [SMILES: O=C1c2ccccc2C(=O)N1Cc1ccc2c(c1)OCO2]

(24) Compound 24 (CAS Registration No. 51626-97-2; Compound 13 described in Bioorganic & Medicinal Chemistry Letters 20, 6644-6648 (2010))

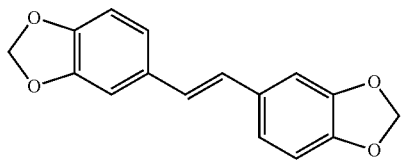 [SMILES: C(=C\c1ccc2c(c1)OCO2)/c1ccc2c(c1)OCO2]

(25) Compound 25 (the compound of Example 7)

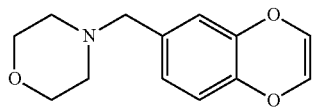 [SMILES: C1=COc2cc(CN3CCOCC3)ccc2O1]

B. Experimental Method

B-1. Experimental Method (1)

A ½ MS medium (agarose: 0.9%; sucrose: 1.5%; Murashige & Skoog plant culture medium×½ concentration) was prepared and autoclaved. Then, the test compounds were separately added thereto at 60 µM and solidified in a plastic petri dish. Arabidopsis seeds (Columbia) were sterilized with ethanol and sown to sprout, followed by observation of conditions of leaves, roots, and stems after sprouting. DMSO alone was added as a solvent for a control.

FIG. 1 shows the state of sprouting on Day 23. The plant growth-promoting agent of the present invention showed excellent plant growth promoting effects. In particular, the compounds, in which the nitrogen-containing heterocyclic ring group represented by NZ in Formula (I) is a saturated nitrogen-containing heterocyclic ring group, showed remarkably excellent plant growth promoting effects. Meanwhile, decreased plant growth promoting activity and/or growth inhibition were confirmed for 1,4-dipiperonylpiperazine (the compound 2), which is a compound substituted with piperonyl groups at the 1- and 4-positions of the piperazine ring, and the compounds 6 and 7, in which the nitrogen-containing heterocyclic ring group represented by NZ in Formula (I) has 3 nitrogen atoms.

Figure 2:
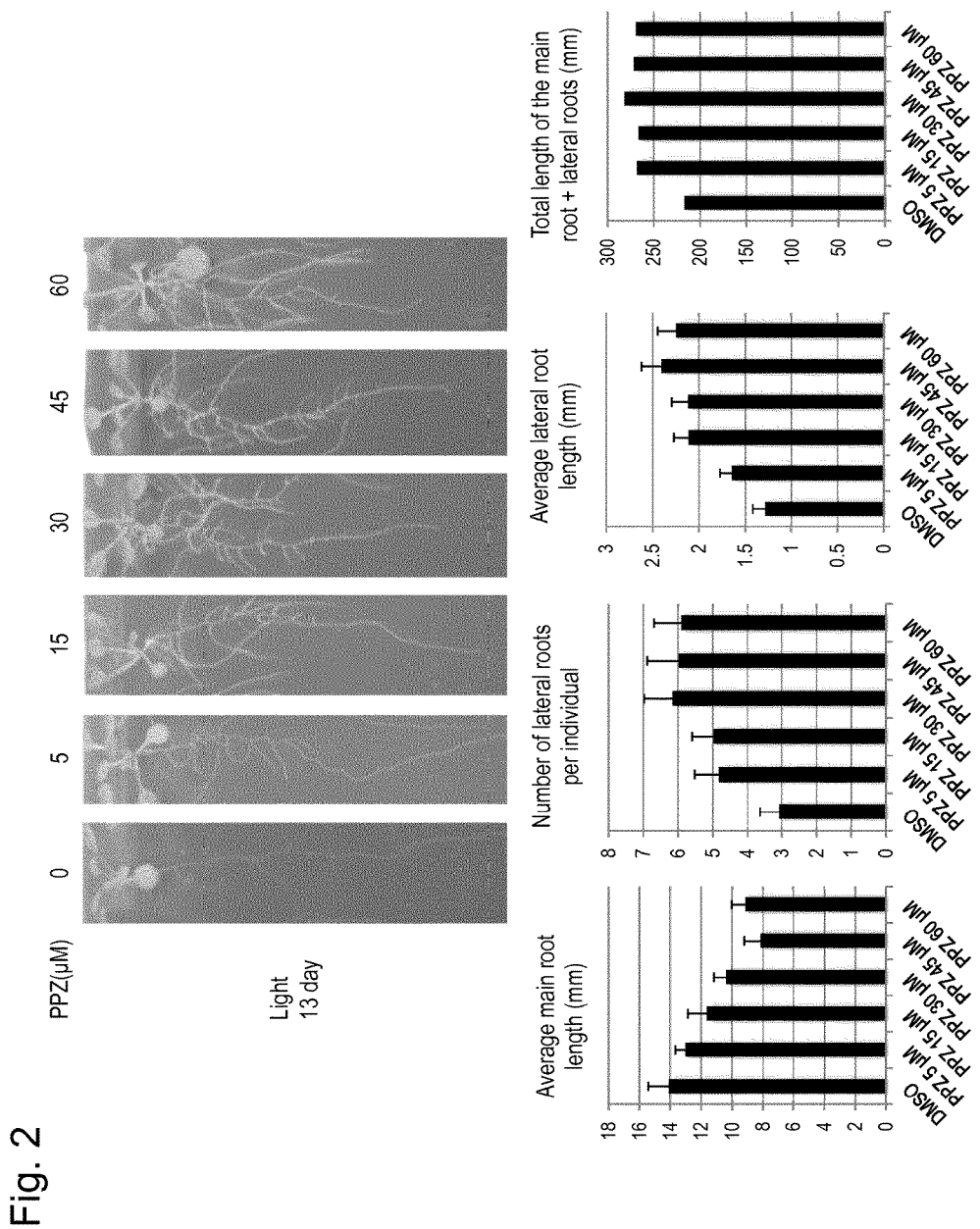
FIG. 2 shows the influence of the plant growth-promoting agent of the present invention upon the development/growth of lateral roots.

FIG. 2 shows conditions of roots on Day 13 of sprouting when culture was conducted using the compound 1 (PPZ) as a test compound at different concentrations of 0 (DMSO alone), 5, 15, 30, 45, and 60 µM under constant light irradiation conditions. The compound 1 (PPZ) was found to have an activity of promoting development/growth of lateral roots in the early growth stage.

Figure 3:
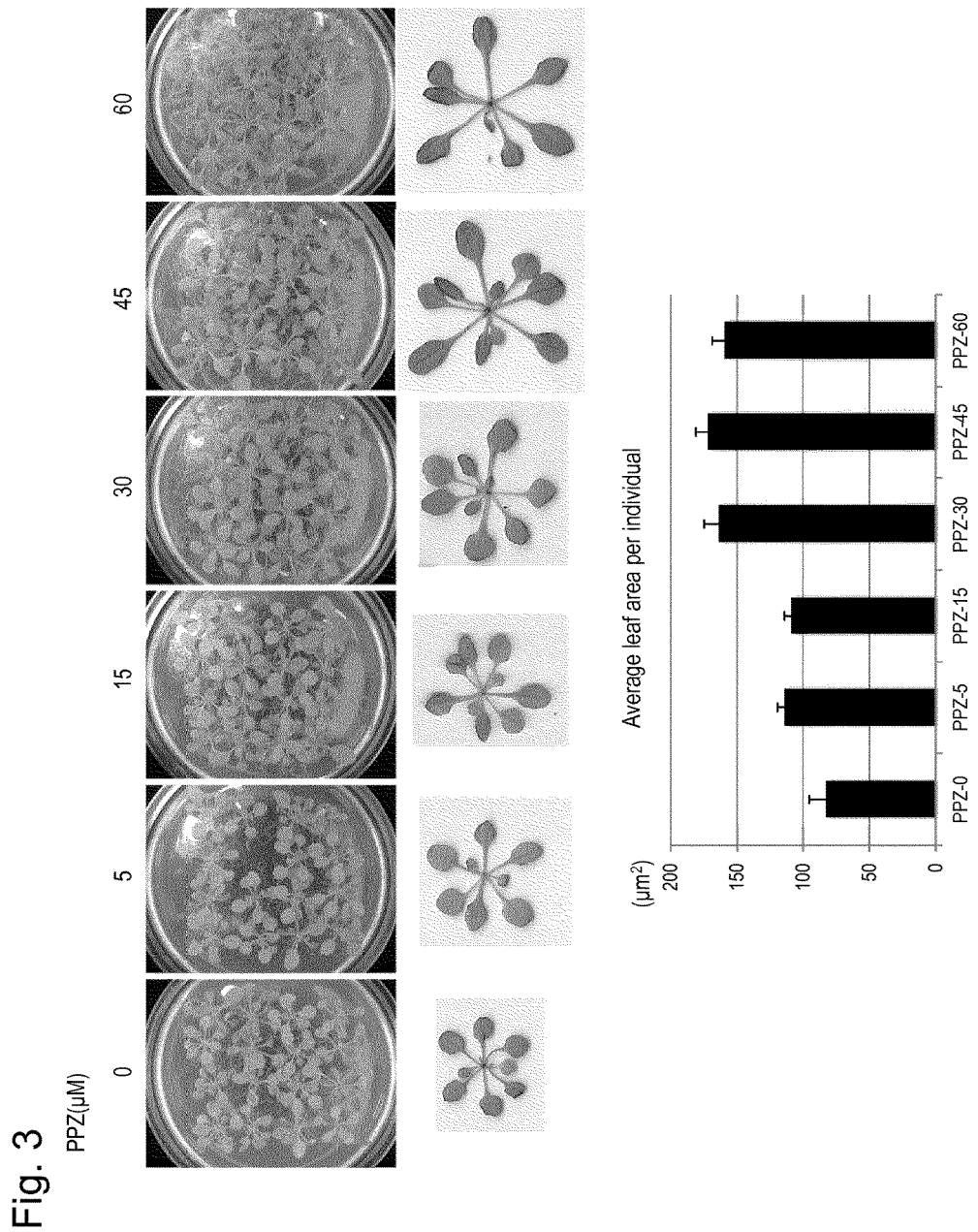
FIG. 3 shows the influence of the plant growth-promoting agent of the present invention upon aerial leaves and petioles.

FIG. 3 shows conditions of leaves on Day 21 of sprouting when culture was conducted using the compound 1 (PPZ) as a test compound at different concentrations of 0 (DMSO alone), 5, 15, 30, 45, and 60 µM. The compound 1 (PPZ) was found to have the activity of promoting growth of aerial leaves and petioles in the late growth stage.

Figure 4:
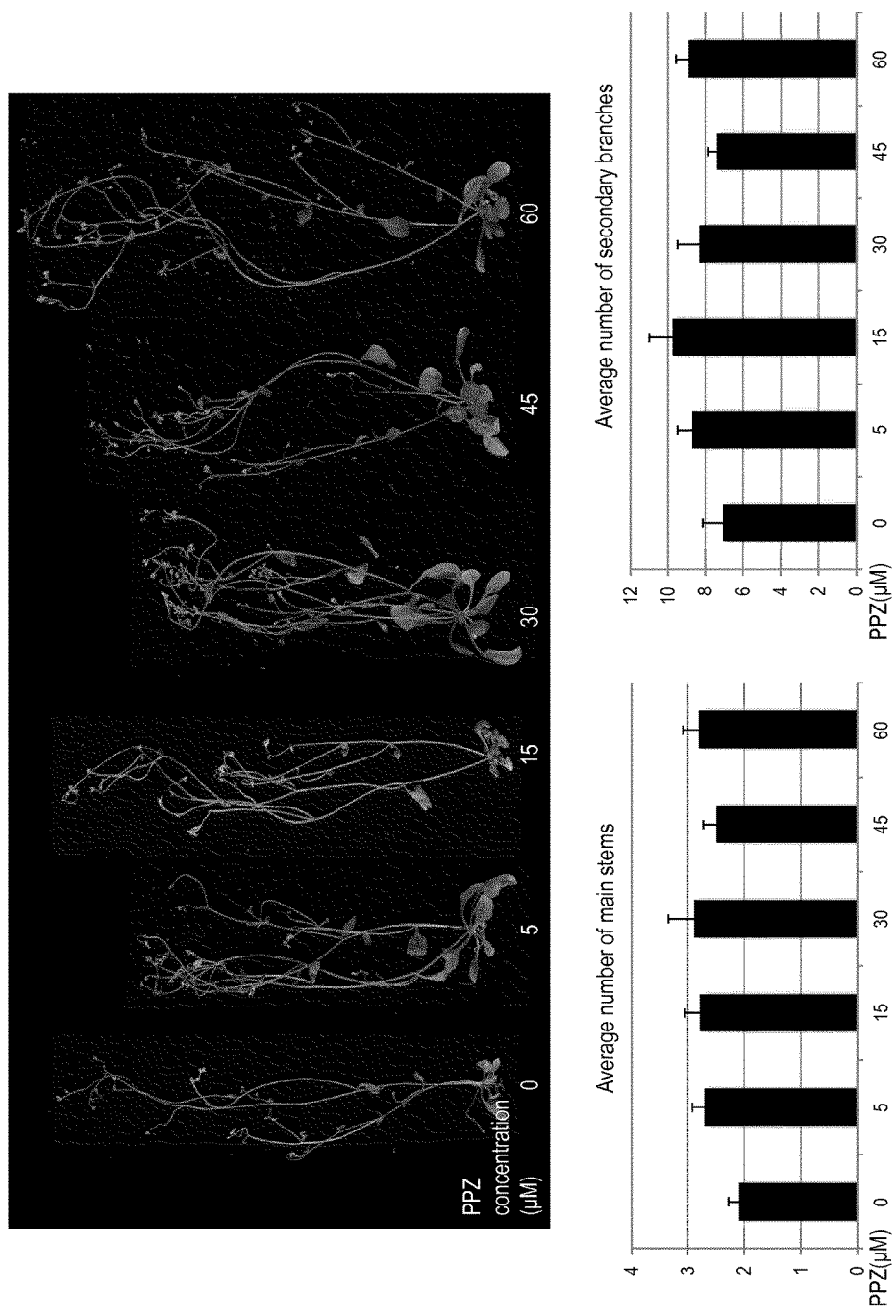
FIG. 4 shows the influence of the plant growth-promoting agent of the present invention upon branching.

FIG. 4 shows the state of branching on Day 35 of sprouting when culture was conducted using the compound 1 (PPZ) as a test compound at different concentrations of 0 (DMSO alone), 5, 15, 30, 45, and 60 µM. The compound 1 (PPZ) was found to have an activity of promoting branching.

Figure 5:
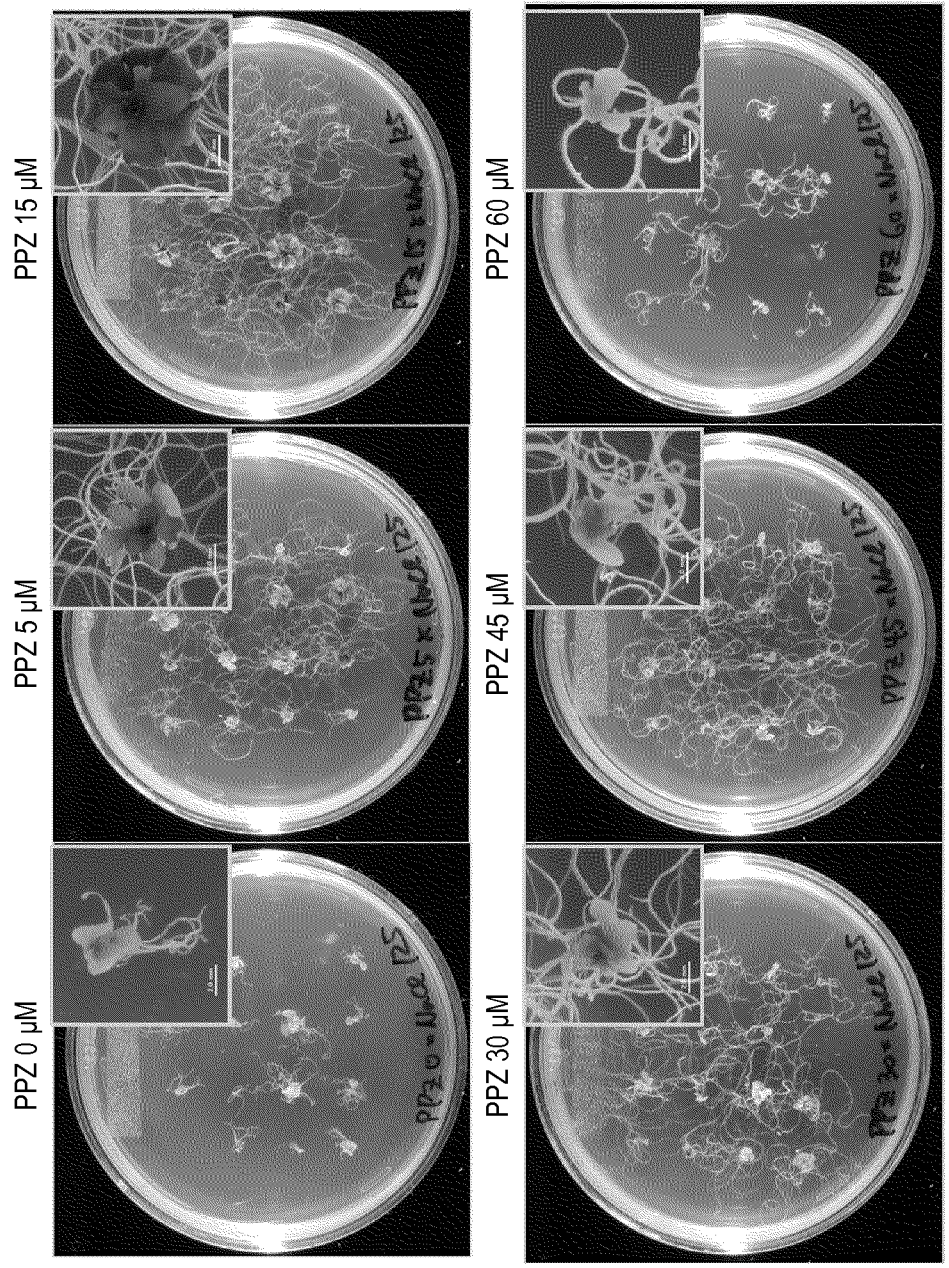
FIG. 5 shows the influence of the plant growth-promoting agent of the present invention upon salt tolerance.

FIG. 5 shows the degree of salt tolerance on Day 21 of sprouting when culture was conducted using the compound 1 (PPZ) as a test compound at different concentrations of 0 (DMSO alone), 5, 15, 30, 45, and 60 µM and a sodium chloride concentration of 125 mM. The compound 1 (PPZ) was found to have an action of enhancing salt tolerance.

The compound 10, which corresponds to a compound represented by Formula (I) wherein $Ar^1$ represents a 3,4-dimethoxyphenyl group, was found to have excellent plant growth promoting effects for elongation of the main root (not shown in figures).

The compound 11 represented by Formula (I) wherein the nitrogen-containing heterocyclic ring group represented by NZ is a 4-methyl-1-piperazinyl group and the compound 12 represented by Formula (Ia) wherein X represents a sulfur atom, were found to have excellent plant growth promoting effects for elongation of stems and roots (not shown in figures).

B-2. Experimental Method (2)

A ½ MS medium (agarose: 0.9%; sucrose: 1.5%; Murashige & Skoog plant culture medium×½ concentration) was prepared and autoclaved. Then, the test compounds were separately added thereto at 0 (DMSO alone), 15, 30, and 60 µM and solidified in a plastic petri dish. Arabidopsis seeds (Columbia) were sterilized with ethanol and sown to sprout, followed by observation of conditions of leaves and roots after sprouting. DMSO alone was added as a solvent for a control.

Figure 6:
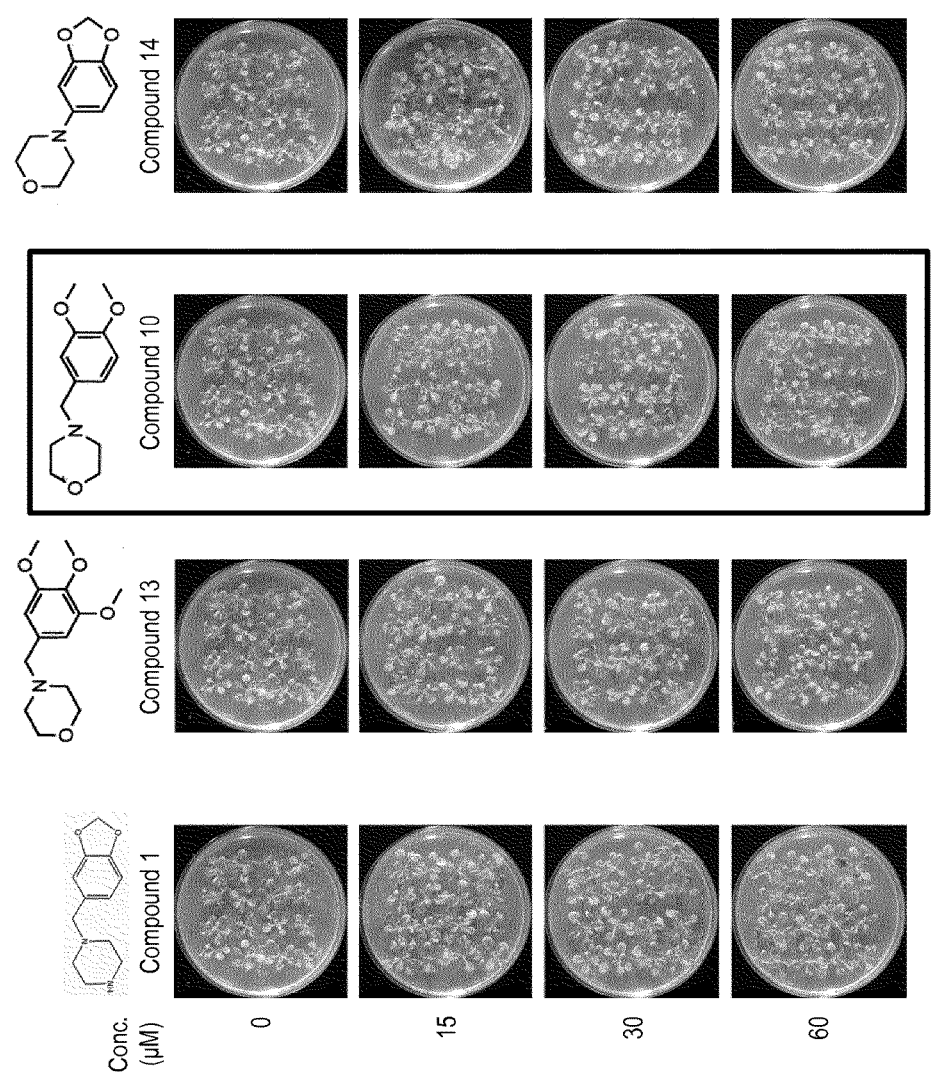
FIG. 6 shows the results of the plant growth promoting activity test using *Arabidopsis*.
Figure 7:
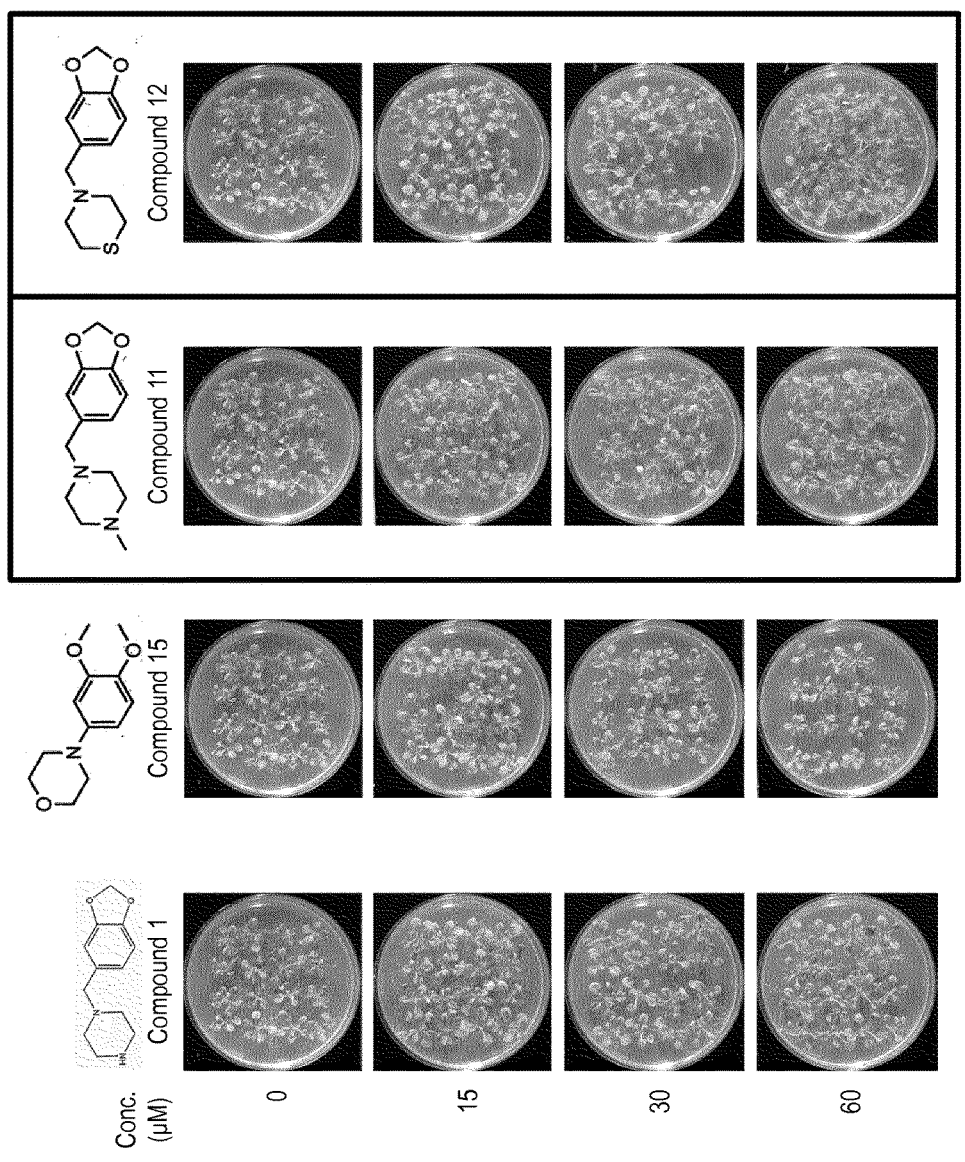
FIG. 7 shows the results of the plant growth promoting activity test using *Arabidopsis*.

FIGS. 6 and 7 show the state of sprouting on Day 22. The plant growth-promoting agent of the present invention was found to have excellent plant growth promoting effects. In particular, the compounds (the compounds 1 and 10 to 12) represented by Formula (Ia) wherein $R^1$ and $R^2$ each represent a hydrogen atom and $Ar^1$ represents a phenyl group substituted with one methylenedioxy group or two methoxy groups were found to have remarkably excellent plant growth promoting effects. Meanwhile, the compound 13 represented by Formula (Ia) wherein $Ar^1$ is a phenyl group substituted with three methoxy groups and the compound 15 represented by Formula (I) wherein n is 0 were found to have weak plant growth promoting effects.

Figure 8:
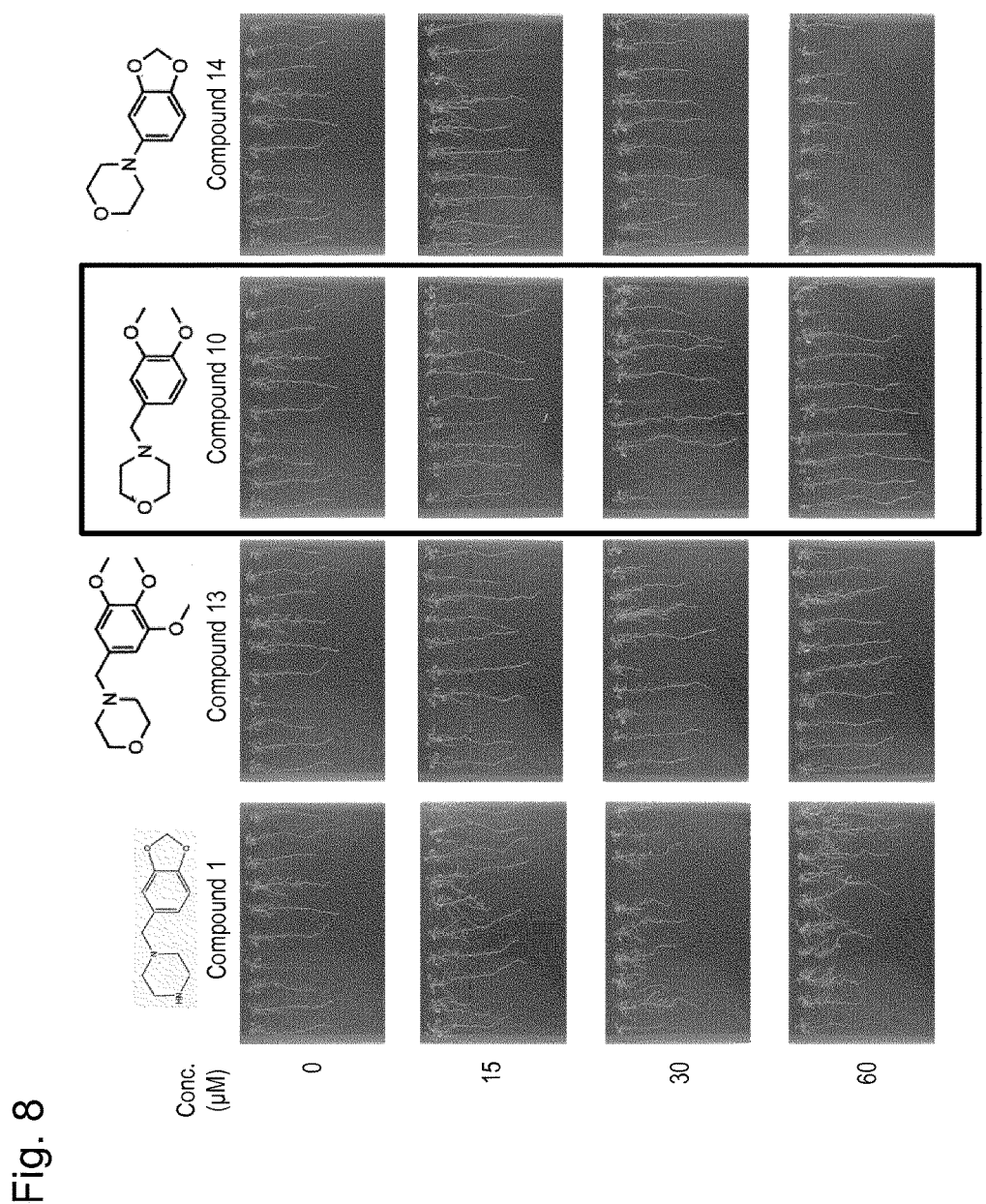
FIG. 8 shows the influence of the plant growth-promoting agent of the present invention upon the development/growth of lateral roots.
Figure 9:
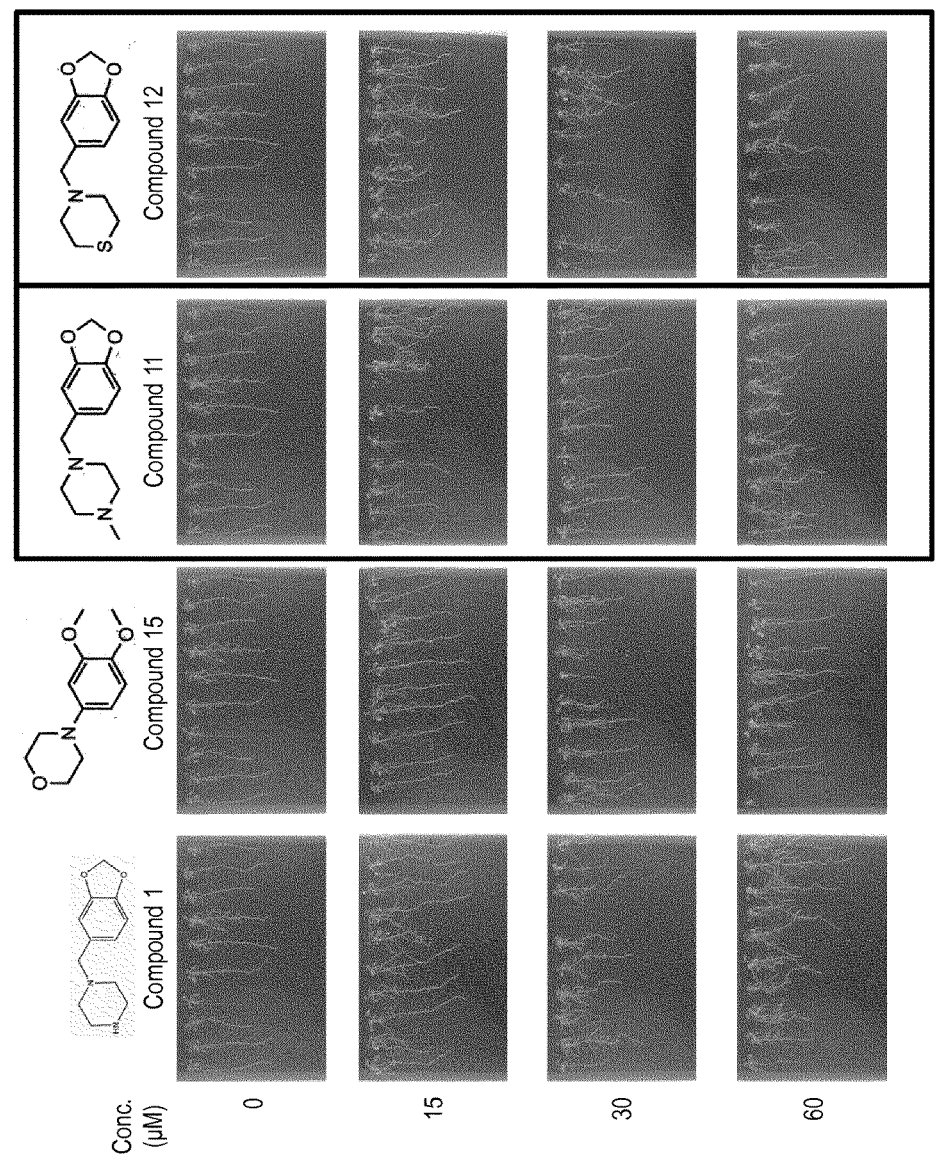
FIG. 9 shows the influence of the plant growth-promoting agent of the present invention upon the development/growth of lateral roots.

FIGS. 8 and 9 show conditions of roots on Day 13 of sprouting when culture was conducted using the compounds 1 and 10 to 15 as test compounds at different concentrations of 0 (DMSO alone), 15, 30, and 60 µM under constant light irradiation conditions. The compounds 1 and 10 to 12 were found to have the activity of promoting development/growth of lateral roots in the early growth stage.

Figure 10:
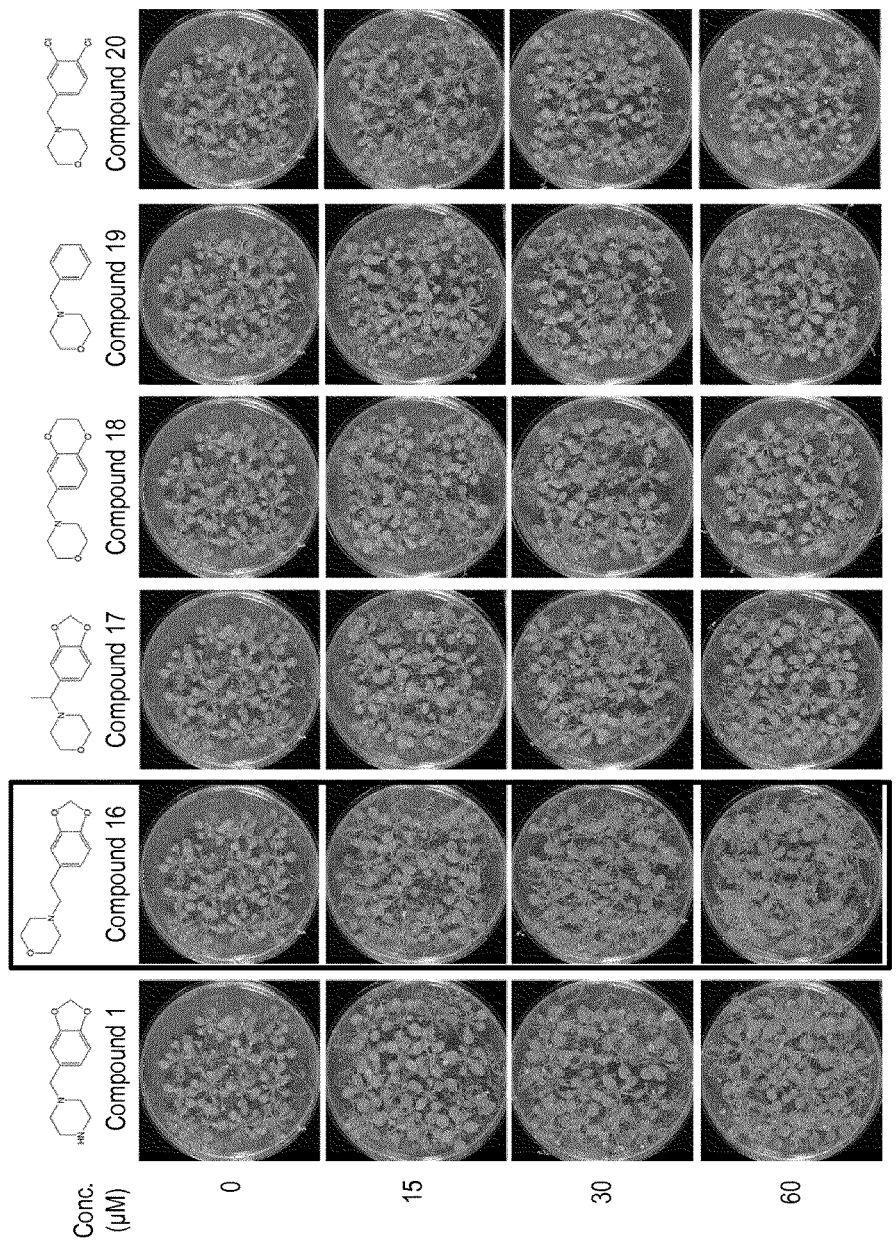
FIG. 10 shows the influence of the plant growth-promoting agent of the present invention upon aerial leaves.
Figure 11:
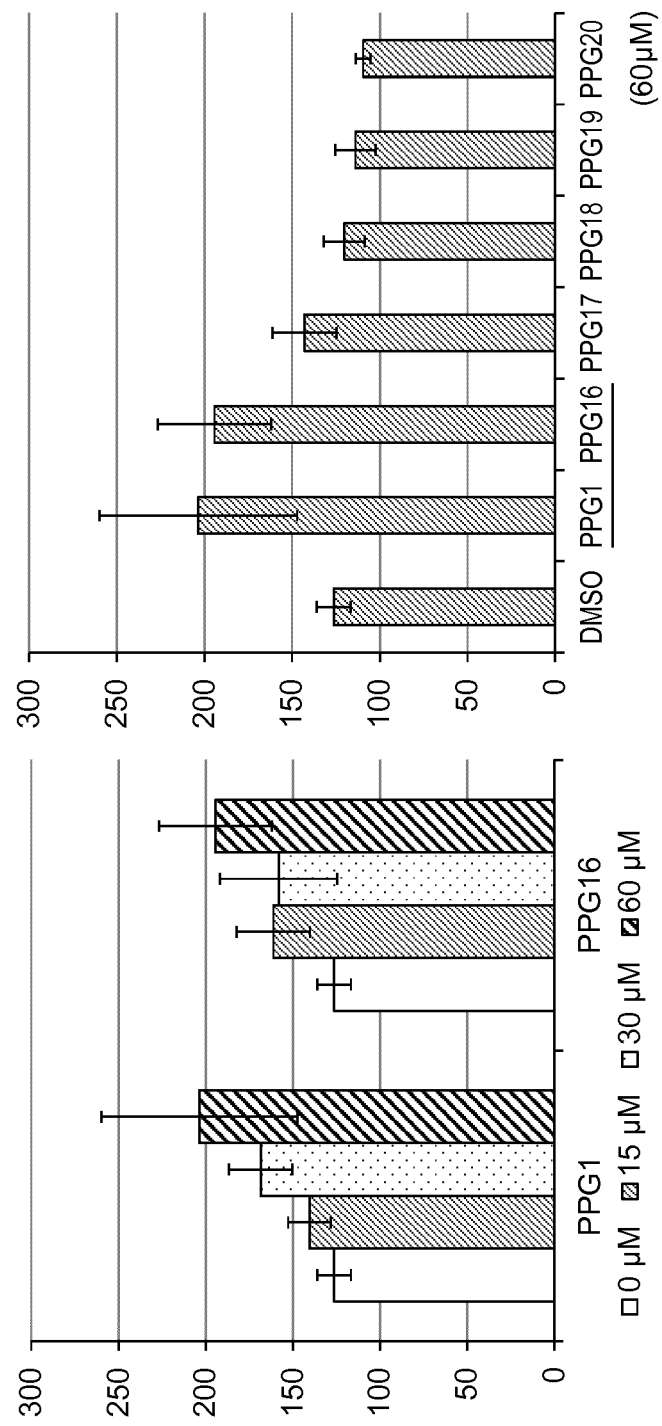
FIG. 11 shows the results of the average leaf area per individual.

FIG. 10 shows conditions of leaves on Day 27 of sprouting when culture was conducted using the compounds 1 and 16 to 20 (PPG1 and PPG16 to PPG20) as test compounds at different concentrations of 0 (DMSO alone), 15, 30, and 60 µM. FIG. 11 shows the results of the average leaf area per individual. The compounds 1 and 16 (PPG1 and PPG16)

were found to have the activity of promoting growth of aerial leaves at the late growth stage.

Figure 12:
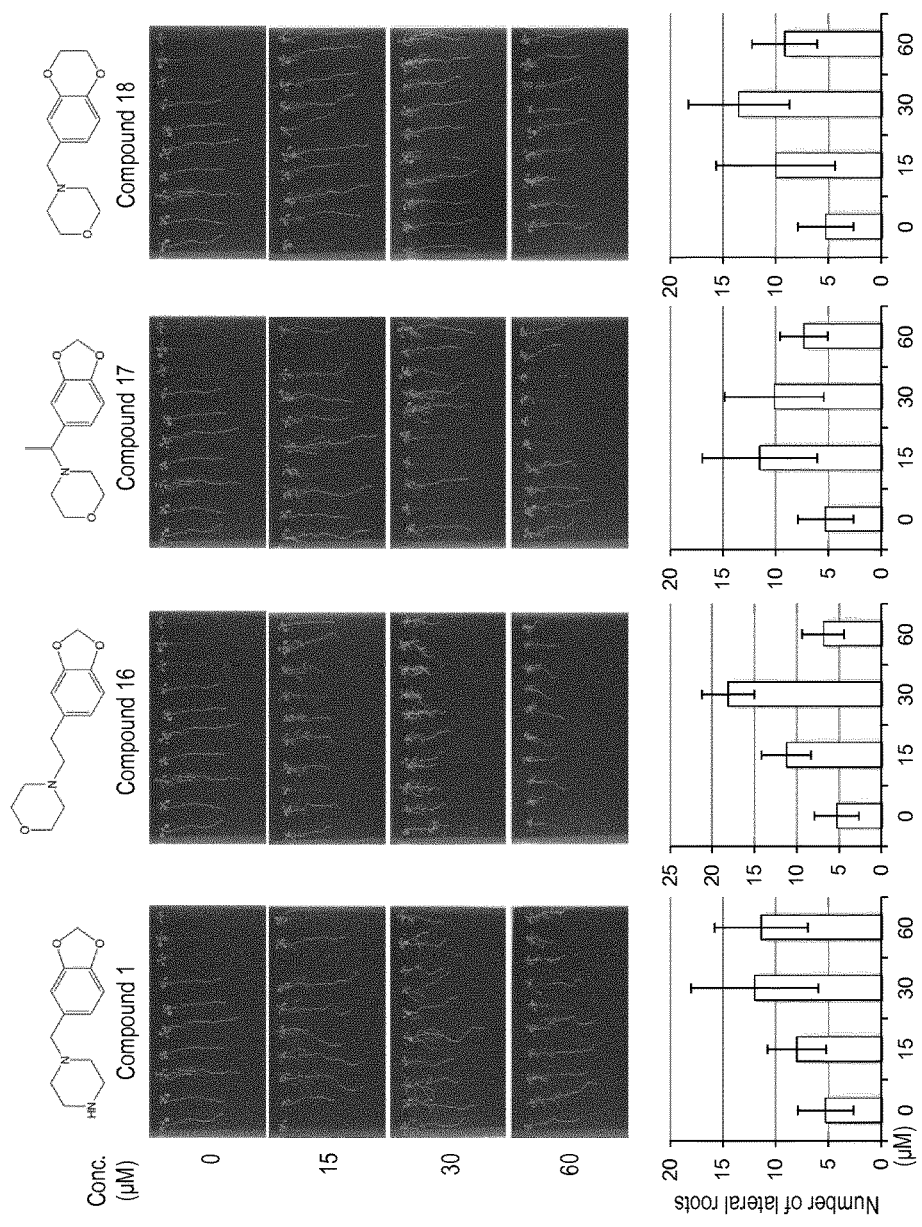
FIG. 12 shows the influence of the plant growth-promoting agent of the present invention upon the development/growth of lateral roots.
Figure 13:
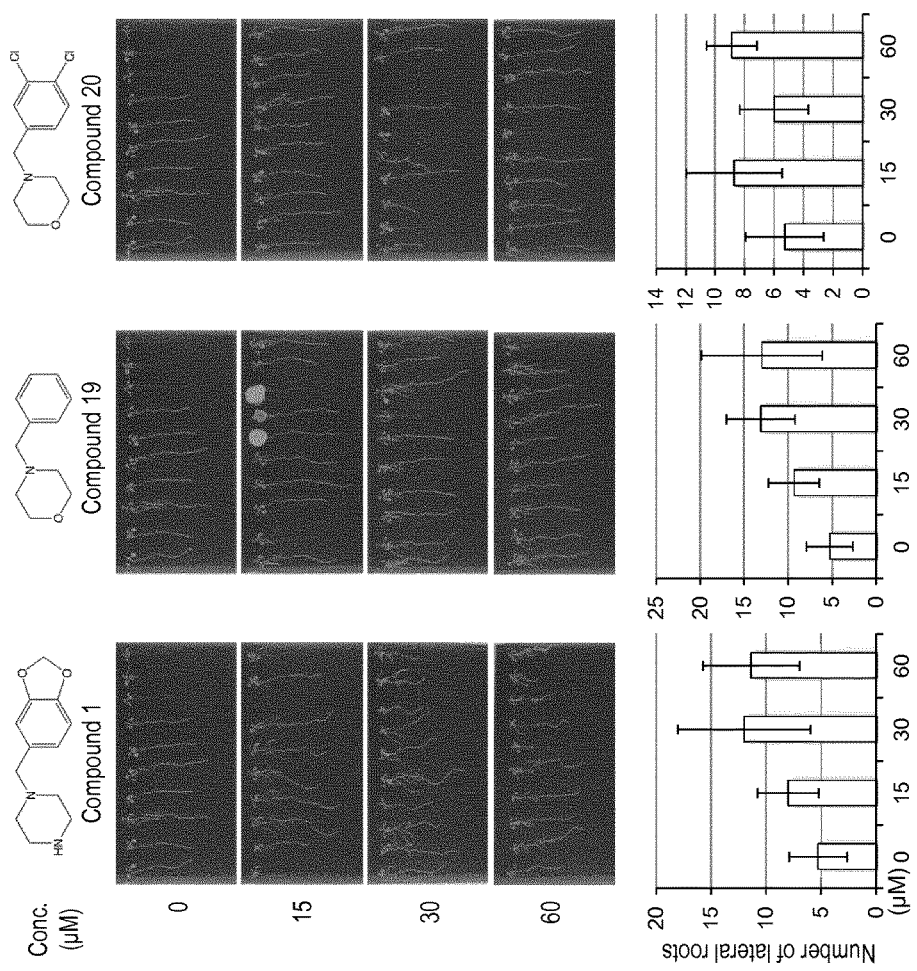
FIG. 13 shows the influence of the plant growth-promoting agent of the present invention upon the development/growth of lateral roots.

FIGS. 12 and 13 show conditions of roots on Day 11 of sprouting when culture was conducted using the compounds 1 and 16 to 20 as test compounds at different concentrations of 0 (DMSO alone), 15, 30, and 60 μM under constant light irradiation conditions. The compounds 1 and 16 to 20 were found to have the activity of promoting development/growth of lateral roots at the early growth stage.

Figure 14:
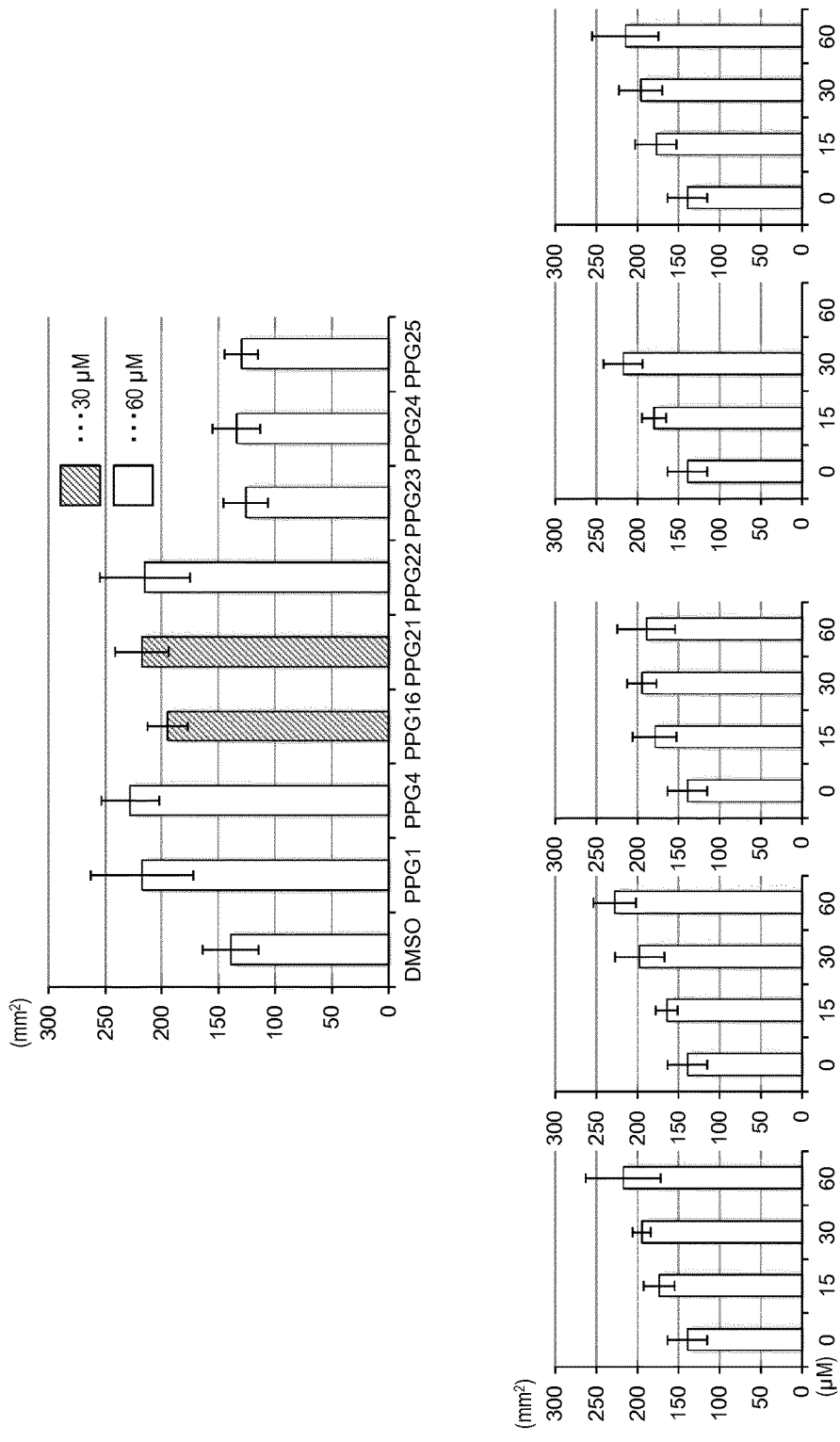
FIG. 14 shows the results of the average leaf area per individual.

FIG. 14 shows the average values obtained by determining the total leaf area per individual for 5 individuals in each experimental plot on day 27 of sprouting under daylight conditions when culture was conducted using the compounds 1, 4, 16, and 21 to 25 (PPG1, PPG4, PPG16, and PPG21 to PPG25) as test compounds at different concentrations of 0 (DMSO alone), 15, 30, and 60 μM.

Figure 15:
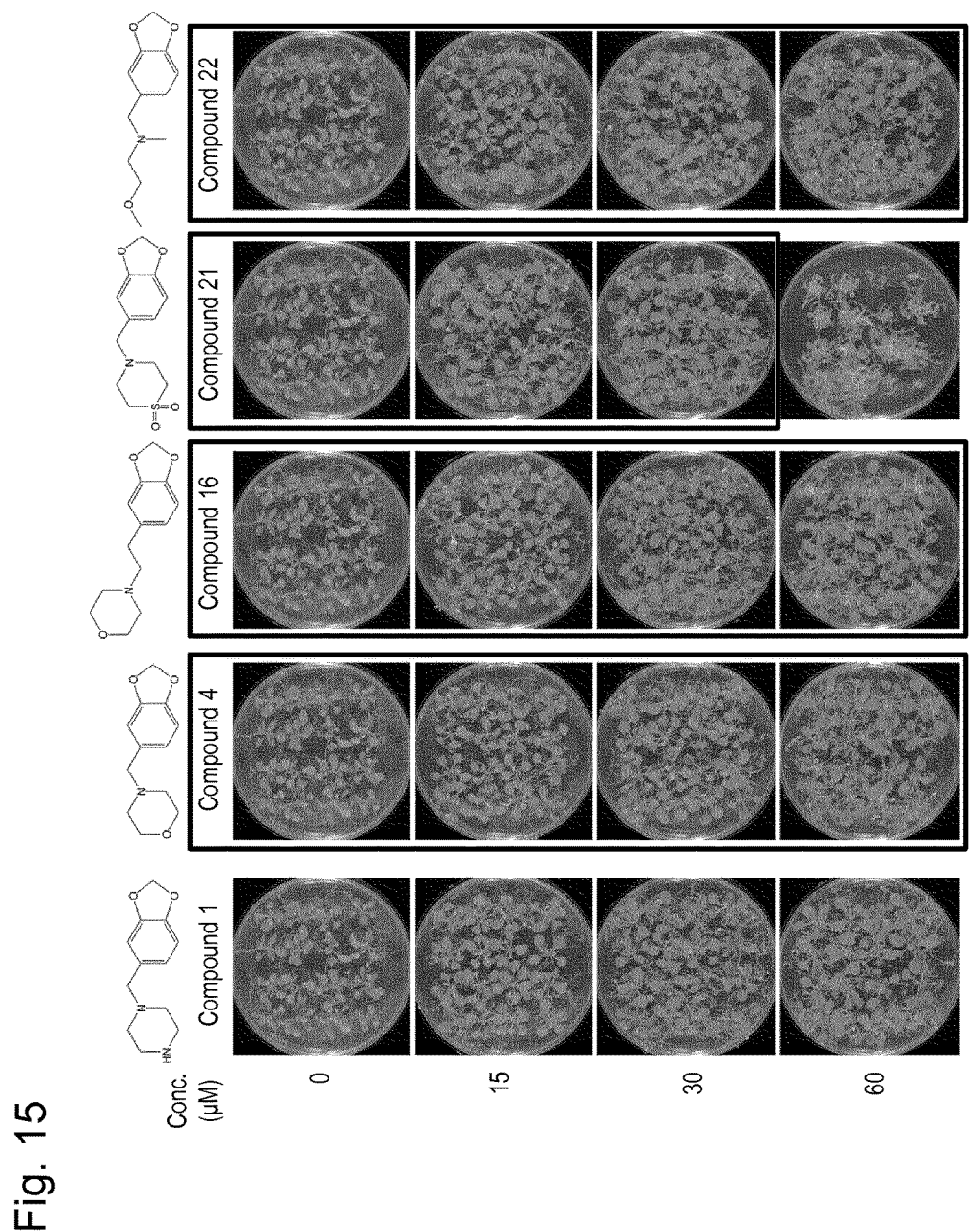
FIG. 15 shows the influence of the plant growth-promoting agent of the present invention upon aerial leaves.
Figure 16:
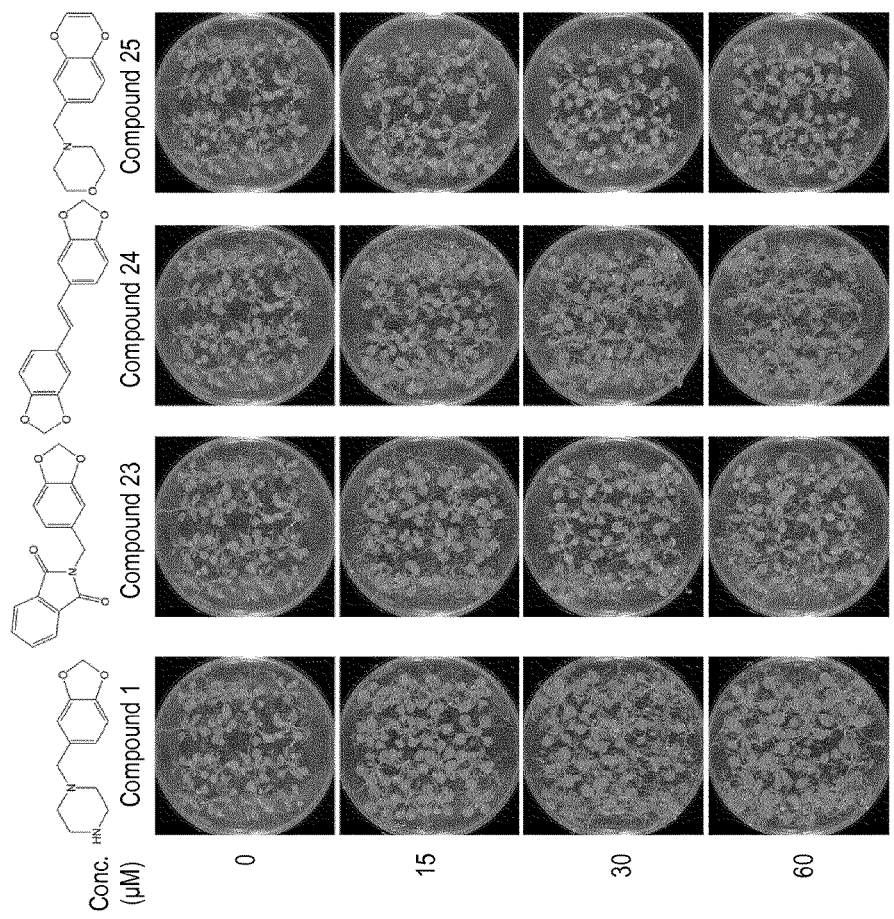
FIG. 16 shows the influence of the plant growth-promoting agent of the present invention upon aerial leaves.

FIGS. 15 and 16 show conditions of leaves on Day 26 of sprouting when culture was conducted using the compounds 1, 4, 16, and 21 to 25 (PPG1, PPG4, PPG16, and PPG21 to PPG25) as test compounds at different concentrations of 0 (DMSO alone), 15, 30, and 60 μM. The compounds 1, 4, 16, 21, and 22 (PPG1, PPG4, PPG16, PPG21, and PPG22) were found to have an activity of promoting the growth of aerial leaves at the late growth stage.

(Example 2) Plant Growth Promoting Effects on Tomato

A ½ MS medium (agarose: 0.9%; sucrose: 1.5%; Murashige & Skoog plant culture medium×½ concentration) was prepared and autoclaved. Then, the compound 1 (PPZ) was added thereto at 0 (DMSO alone), 5, 15, and 30 μM and solidified in a plastic pot. Tomato seeds (Micro-Tom) were sterilized with hypochlorous acid and sown to sprout, followed by observation of conditions of leaves and stems after sprouting. DMSO alone was added as a solvent for a control.

Figure 17:
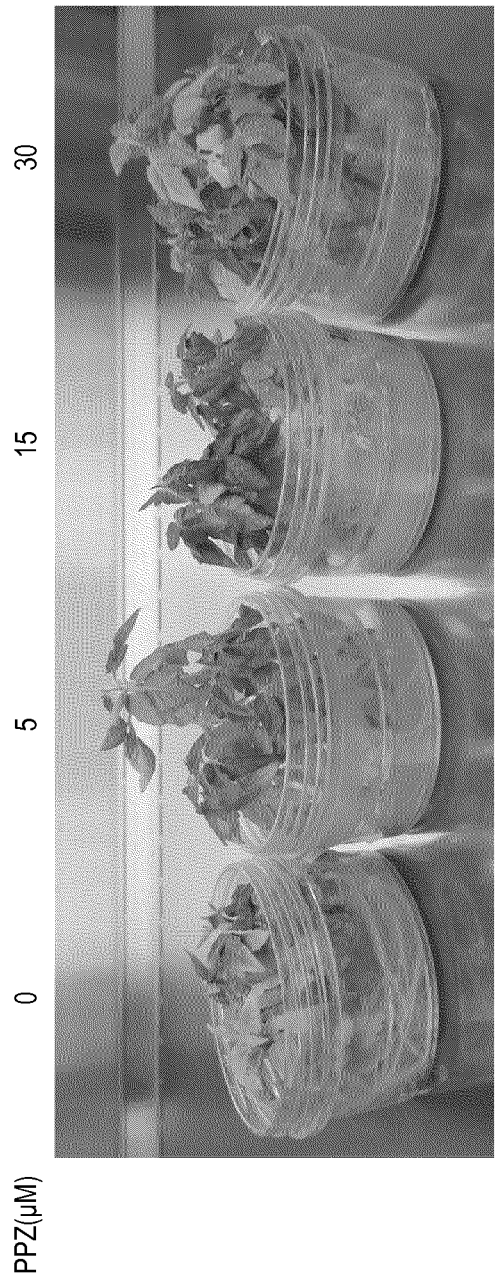
FIG. 17 shows the influence of the plant growth-promoting agent of the present invention upon aerial leaves and stems of tomato.

FIG. 17 shows the state of sprouting on Day 73 of sprouting. The compound 1 (PPZ) was found to have the activity of promoting the growth of aerial leaves and stems of tomato.

(Example 3) Plant Growth Promoting Effects Upon Rice

A plant pot containing rice culture soil was prepared and rice (Nipponbare) was sown therein. Rice was raised with distilled water until Day 7 of sprouting. Rice was allowed to absorb distilled water containing the compound 1 (PPZ) at a concentration of 0 (DMSO alone), 15, or 30 μM from the bottom of the pot from Day 7 of sprouting. Water used was discarded every 7 days and replaced by fresh water. Rice was photographed and the plant length of rice was measured on Day 21 of sprouting or Day of 14 from the start of treatment.

Figure 18:
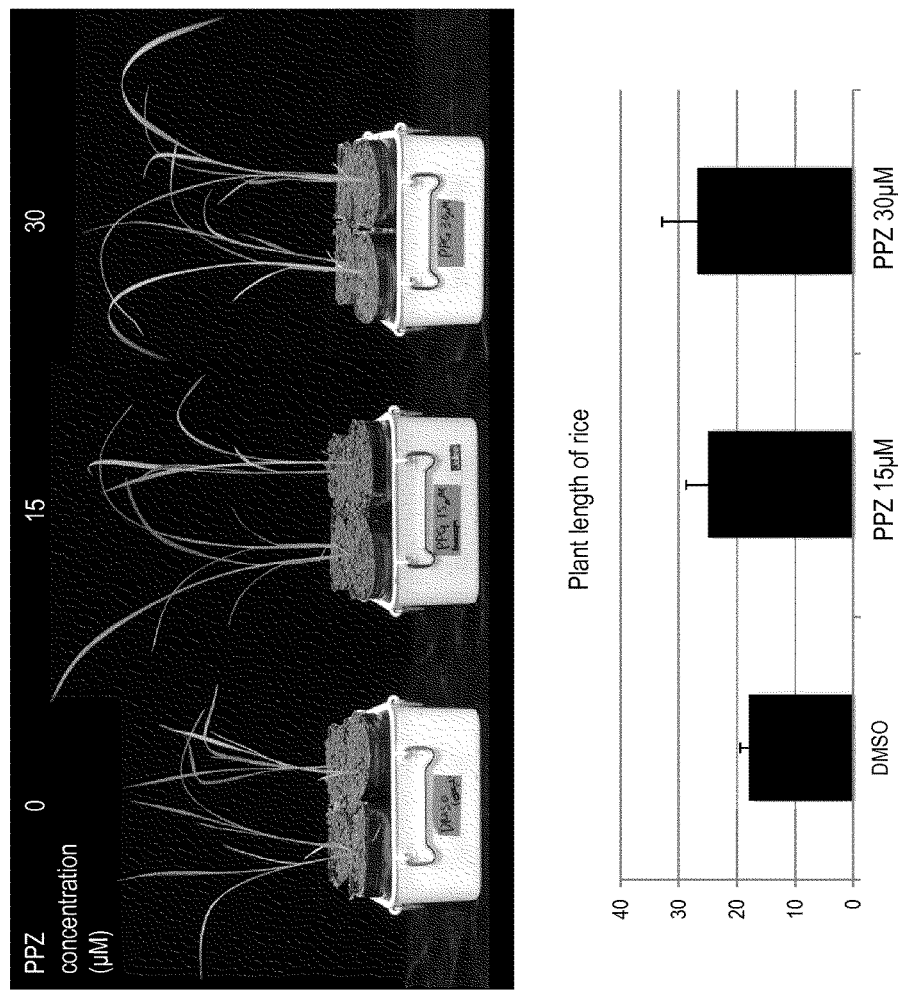
FIG. 18 shows the influence of the plant growth-promoting agent of the present invention upon aerial leaves and stems of rice.

FIG. 18 shows the results. The compound 1 (PPZ) was found to have the activity of promoting the growth of aerial leaves and stems of rice.

(Example 4) Synthesis of Compound 16

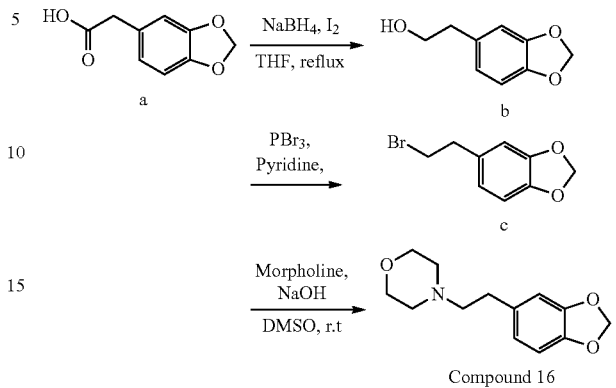

(1) Synthesis of Compound b

Sodium borohydride (1.98 g) and THF (75 ml) were introduced into an eggplant-shaped flask and ice-cooled. A THF solution (25 ml) of the above compound a (2.03 g) was added at once thereto, and then a THF solution (15 ml) of iodine (5.72 g) was slowly added dropwise thereto for 30 minutes. Thereafter, the mixture was heated to reflux during overnight stirring. The mixture was ice-cooled and methanol was slowly added dropwise thereto until foaming disappeared so that the reaction was terminated. A certain volume of THF was removed from the reaction solution using an evaporator. Dichloromethane was added to the reaction solution. The resulting solution was washed with a 1M-sodium hydroxide aqueous solution and saturated saline in that order, dehydrated with sodium sulfate, and concentrated. The concentrate was purified by silica gel column chromatography (Wakosil™ C-300) using chloroform-methanol as an eluent. Thus, the compound b was obtained (yield: 1.09 g; yield rate: 59%)

(2) Synthesis of Compound 16

The compound b (1.1 g), dichloromethane (15 ml), and pyridine (500 μl) were introduced into an eggplant-shaped flask and ice-cooled. Phosphorus tribromide (1.0 ml) was slowly added thereto. Five minutes later, the mixture was adjusted to room temperature and stirred for 2 hours. The reaction was terminated using water, followed by extraction with dichloromethane. Thereafter, the reaction solution was washed with saturated saline, dehydrated with sodium sulfate, and concentrated. Thus, the compound c was obtained. The obtained compound was directly used for the next reaction.

Sodium hydroxide (0.48 g) and DMSO (15 ml) were introduced into an eggplant-shaped flask and stirred for 30 minutes. Then, morpholine (1.05 ml) was added thereto. The solution was ice-cooled, and the compound c was added thereto. The mixture was immediately stirred for 5 minutes and then stirred overnight at room temperature. Water was added to terminate the reaction of the reaction solution, followed by extraction with ethyl acetate. Subsequently, the extract was washed twice with water and then with saturated saline, dehydrated with sodium sulfate, and concentrated. The concentrate was purified by silica gel column chromatography (Wakosil™ C-300) using ethyl acetate-methanol as an eluent. Thus, the compound 16 was obtained (yield: 200 mg; yield rate: 14%).

$^1$H NMR (CDCl$_3$, 500 MHz): δ=2.50 (4H, br), 2.54 (2H, m), 2.71 (2H, m), 3.37 (4H, t, J=5.0 Hz), 5.91 (2H, s), 6.64 (1H, dd, J=1.5, 8.0 Hz), 6.70 (1H, d, J=2.0 Hz), 6.72 (1H, d, J=8.0 Hz)

(Example 5) Synthesis of Compound 17

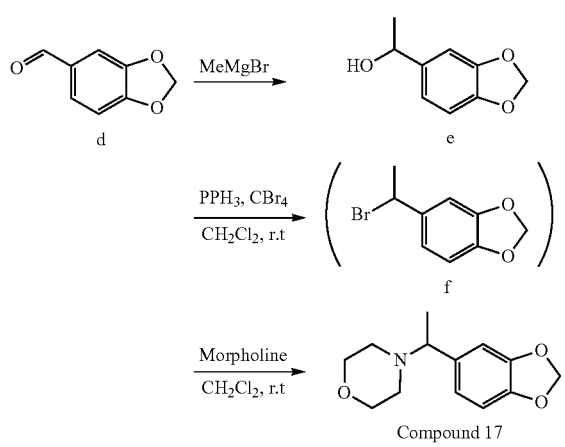

(1) Synthesis of Compound e

The above compound d and THF (40 ml) were introduced into an eggplant-shaped flask and cooled to −78° C. in a nitrogen atmosphere. A THF solution (0.92 mol/l, 21 ml) containing methylmagnesium bromide was slowly added dropwise to the solution, followed by stirring for 2 hours. Water was slowly added to terminate the reaction of the reaction solution. The reaction solution was adjusted to ordinary temperature, and a certain volume of THF was removed therefrom using an evaporator, followed by extraction with ethyl acetate. Subsequently, the extract was washed with water and saturated saline in that order, dehydrated with sodium sulfate, and concentrated. The concentrate was purified by silica gel column chromatography (Wakosil™ C-300) using hexane-ethyl acetate as an eluent. Thus, the compound e was obtained (yield: 2.03 g; yield rate: 86%).

(2) Synthesis of Compound 17

The compound e (205 mg), dichloromethane (4.0 ml), triphenylphosphine (0.98 g), and carbon tetrabromide (1.21 g) were added to an eggplant-shaped flask and stirred at room temperature for 5 hours. When there was no further change observed by TLC, morpholine (3.65 ml) was added, followed by overnight stirring at room temperature. The reaction solution was extracted with ethyl acetate. Subsequently, the extract was washed with water and saturated saline in that order, dehydrated with sodium sulfate, and concentrated. The concentrate was purified by silica gel column chromatography (Wakosil™ C-300) using hexane-ethyl acetate as an eluent. Thus, the compound 17 was obtained (yield: 90.7 mg; yield rate: 31%).

$^1$H NMR (CDCl$_3$, 500 MHz): δ=1.30 (3H, d, J=6.0 Hz), 2.33-2.45 (4H, m), 3.21 (1H, q, J=6.5 Hz), 3.68 (4H, t, J=5.0 Hz), 5.93 (2H, d, J=1.5 Hz), 6.71-6.75 (2H), 6.86 (1H, s)

(Example 6) Synthesis of Compound 22

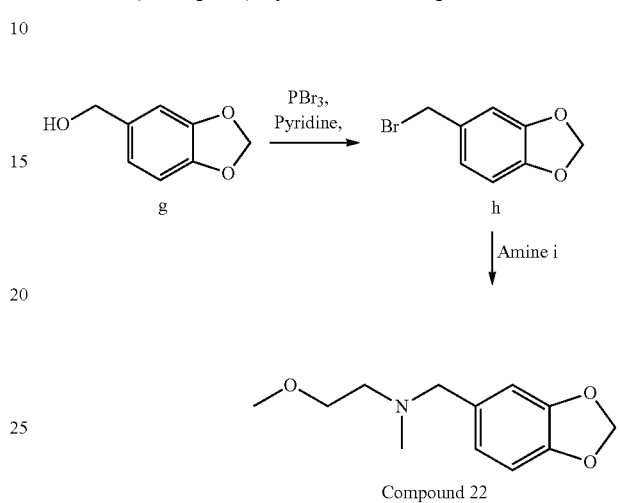

Piperonyl alcohol (compound g) (1 g, 1 eq), dichloromethane (15 ml), and pyridine (1 eq) were introduced into an eggplant-shaped flask and ice-cooled. Phosphorus tribromide (0.5 eq) was slowly added thereto. Five minutes later, the mixture was adjusted to room temperature and stirred for 2 hours. Water was added to terminate the reaction, followed by extraction with dichloromethane. Subsequently, the extract was washed with saturated saline, dehydrated with sodium sulfate, and concentrated. Thus, the compound h was obtained. The obtained compound was directly used for the next reaction.

Sodium hydroxide (2 eq) and DMSO (15 ml) were introduced into an eggplant-shaped flask and stirred for 30 minutes. Then, N-(2-methoxyethyl)methane amine was added as the above amine i. The resulting solution was ice-cooled, and the compound h was added thereto. The solution was immediately stirred for 5 minutes and then stirred overnight at room temperature. Water was added to terminate the reaction of the reaction solution, followed by extraction with ethyl acetate. Subsequently, the extract was washed with water and saturated saline in that order, dehydrated with sodium sulfate, and concentrated. The concentrate was purified by silica gel column chromatography (Wakosil™ C-300) using hexane-ethyl acetate as an eluent. Thus, the compound 22 was obtained (yield: 971 mg; yield rate: 66%).

$^1$H NMR (CDCl$_3$, 500 MHz): δ=2.24 (3H, s), 2.58 (2H, t, J=8.0 Hz), 3.34 (3H, s), 3.46 (2H, s), 3.50 (2H, t, J=6.0 Hz), 5.93 (2H, s), 6.73 (2H, d, J=1.5 Hz), 6.84 (1H, s)

In addition, the compounds 1 to 9, 11, and 12 were synthesized in the above manner except that an amine other than N-(2-methoxyethyl)methane amine was used as the amine i.

(Example 7) Synthesis of Compound 25

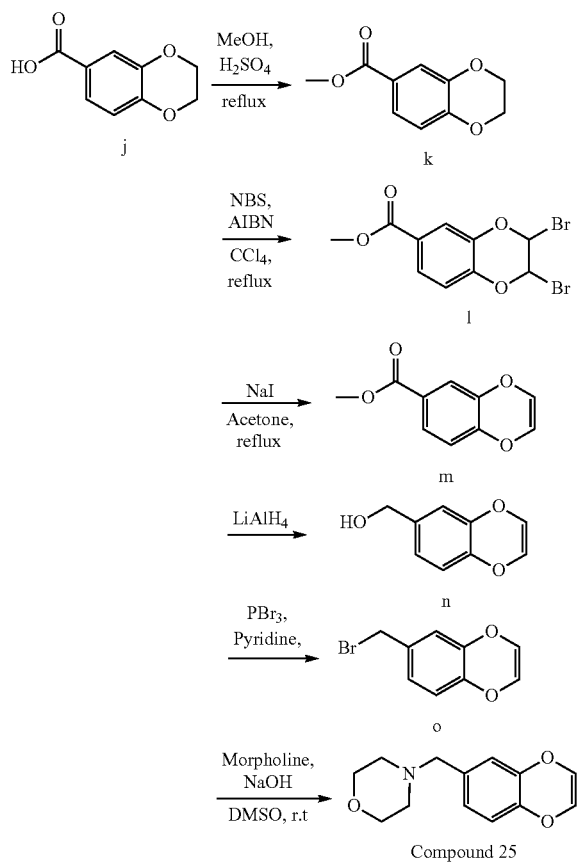

(1) Synthesis of Compound k

A mixed solution of the compound j (1.5 g) and sulfuric acid (2.0 ml)/methanol (17 ml) was introduced into an eggplant-shaped flask and heated overnight to reflux. The reaction solution was extracted with ethyl acetate. Then, the extract was washed with saturated saline, dehydrated with sodium sulfate, and concentrated. The concentrate was purified by silica gel column chromatography (Wakosil™ C-300) using hexane-ethyl acetate as an eluent. Thus, the compound k was obtained (yield: 1.69 g; yield rate: 52%).

(2) Synthesis of Compound l

The compound k (2.01 g), NBS (8.48 g), and carbon tetrachloride (125 ml) were introduced to an eggplant-shaped flask. Then, AIBN (340 mg) was added thereto in a nitrogen atmosphere and heated to reflux for 44 hours. The reaction solution was extracted with chloroform. Subsequently, the extract was washed with saturated saline, dehydrated with sodium sulfate, and concentrated. The concentrate was purified by silica gel column chromatography (Wakosil™ C-300) using chloroform alone as an eluent. Thus, the compound l was obtained (yield: 2.64 g; yield rate: 73%).

(3) Synthesis of Compound m

The compound l (2.64 g), acetone (75 ml), and sodium iodide (5.63 g) were introduced to an eggplant-shaped flask and heated to reflux for 3 hours. The reaction solution was extracted using dichloromethane. Then, the extract was washed with saturated saline, dehydrated with sodium sulfate, and concentrated. The concentrate was purified by silica gel column chromatography (Wakosil™ C-300) using hexane-ethyl acetate as an eluent. Thus, the compound m was obtained (yield: 1.03 g; yield rate: 72%).

(4) Synthesis of Compound n

A THF solution (1.0 ml) containing 1M-lithium aluminium hydride and THF (1.0 ml) were introduced to an eggplant-shaped flask and ice-cooled. A THF solution (2.0 ml) containing the compound m (101 mg) was slowly added to the solution, immediately followed by stirring for 30 minutes. Water (35 μl), 1N—NaOH (70 μl), and water (100 μl) were added to the reaction solution in that order. The resulting solution was diluted with ethyl acetate, filtered through Celite, and concentrated. The concentrate was directly used for the next reaction (crude yield: 86.4 mg; crude yield rate: 101%).

(5) Synthesis of Compound 25

The compound n (86.4 mg), dichloromethane (1.0 ml), and pyridine (42 μl) were introduced into an eggplant-shaped flask and ice-cooled. Phosphorus tribromide (25 μl) was slowly added thereto and immediately stirred for 30 minutes. Water was added to terminate the reaction of the reaction solution, followed by extraction with ethyl acetate. Subsequently, the extract was washed with saturated saline, dehydrated with sodium sulfate, and concentrated. Thus, the compound o was obtained. The obtained compound was directly used for the next reaction.

Sodium hydroxide (97 mg) and DMSO (1.6 ml) were introduced into an eggplant-shaped flask and stirred for 30 minutes. Then, morpholine (100 μl) was added thereto. The resulting solution was ice-cooled, and the compound o (total amount) was added thereto. The solution was immediately stirred for 5 minutes and then stirred overnight at room temperature. The reaction solution was extracted with ethyl acetate. Subsequently, the extract was washed with saturated saline, dehydrated with sodium sulfate, and concentrated. The concentrate was purified by silica gel column chromatography (Wakosil™ C-300) using hexane-ethyl acetate as an eluent. Thus, the compound 25 was obtained (yield: 35.3 g; yield rate: 29%).

$^1$H NMR (CDCl$_3$, 500 MHz): δ=2.40 (4H, br), 3.31 (2H, s), 3.69 (4H, t, J=5.0 Hz), 5.85 (2H, s), 6.54 (1H, d, J=8.0 Hz), 6.62 (1H, d, J=2.0 Hz), 6.74 (1H, dd, J=2.0, 8.0 Hz), 6.84 (1H, s)

All publications, patents, and patent applications cited herein are incorporated herein by reference in their entirety.

The invention claimed is:

1. A method for promoting plant growth, comprising bringing a plant, plant cells, a plant tissue, or plant seeds into contact with a plant growth-promoting agent comprising a compound represented by Formula (I) or a salt thereof:

wherein Ar¹ represents a substituted phenyl group wherein at least one substituent of the substituted phenyl group is selected from $C_{1-6}$ alkoxy groups, substituted or unsubstituted $C_{1-3}$ alkylenedioxy groups and halogen atoms;

NZ represents a substituted or unsubstituted nitrogen-containing heterocyclic ring group having 1 or 2 nitrogen atoms, which is bound to $C(R^1)(R^2)$ or Ar¹ via a nitrogen atom, or a group represented by Formula (II):

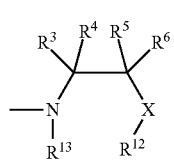

(II)

wherein X represents $NR^{11}$ (where $R^{11}$ represents a hydrogen atom or a substituted or unsubstituted $C_{1-3}$-alkyl group), an oxygen atom, a sulfur atom, —$SO_2$—, —SO—, a methylene group, or a direct bond;

$R^3$, $R^4$, $R^5$ and $R^6$ each represent a hydrogen atom or a methyl group;

$R^{12}$ and $R^{13}$ each represent a hydrogen atom or a substituted or unsubstituted $C_{1-3}$-alkyl group;

n is 0, 1, or 2; and $R^1$ and $R^2$ each represent a hydrogen atom, a substituted or unsubstituted $C_{1-3}$-alkyl group, a cyano group, or a carboxyl group, $R^1$ and $R^2$ may together form an oxo group, and when n is 2, $R^1$ or $R^2$ may be the same or different.

2. The method according to claim 1, wherein the compound represented by Formula (I) or a salt thereof is a compound represented by Formula (Ia) or a salt thereof:

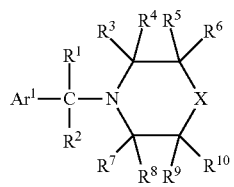

(Ia)

wherein Ar¹, $R^1$, and $R^2$ are as defined above with respect to Formula (I) in claim 1;

X represents $NR^{11}$ (where $R^{11}$ represents a hydrogen atom or a substituted or unsubstituted $C_{1-3}$-alkyl group), an oxygen atom, a sulfur atom, —$SO_2$—, —SO—, a methylene group, or a direct bond; and $R^3$, $R^4$, $R^5$, $R^6$, $R^7$, $R^8$, $R^9$, and $R^{10}$ each represent a hydrogen atom or a methyl group.

3. The method according to claim 1, wherein $R^1$ and $R^2$ each represent a hydrogen atom in Formula (I).

4. The method according to claim 2, wherein $R^1$ and $R^2$ each represent a hydrogen atom in Formula (Ia).

5. The method according to claim 1, wherein Ar¹ is a phenyl group substituted with one methylenedioxy group or one or two methoxy groups in Formula (I).

6. The method according to claim 1, wherein NZ represents a saturated nitrogen-containing heterocyclic ring group in Formula (I).

7. The method according to claim 1, wherein n is 1 or 2 in Formula (I).

8. The method according to claim 1, wherein NZ is selected from the group consisting of a 1-piperazinyl group, a 1-pyrrolidinyl group, a piperidino group, a morpholino group, a 1,1-dioxidethiomorpholino group, and a perhydro-1,4-thiazine-4-yl group, which may be substituted with at least one substituent.

9. The method according to claim 1, wherein Ar' represents a substituted phenyl group represented by the following formula:

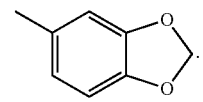

10. The method according to claim 1, wherein the plant growth-promoting agent is mixed with a fertilizer.

11. The method according to claim 10, wherein Ar¹ represents a substituted phenyl group represented by the following formula:

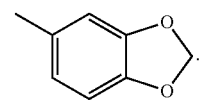

12. The method according to claim 1, wherein the plant growth-promoting agent is mixed with culture soil.

13. The method according to claim 12, wherein the culture soil further comprises at least one material selected from the group consisting of soil, sand, cotton and sponge.

14. The culturing medium method according to claim 12, wherein Ar¹ represents a substituted phenyl group represented by the following formula:

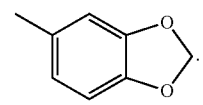

* * * * *